US011298019B2

(12) United States Patent
Hirose et al.

(10) Patent No.: US 11,298,019 B2
(45) Date of Patent: Apr. 12, 2022

(54) OPHTHALMOLOGIC APPARATUS AND METHOD FOR CONTROLLING THE SAME

(71) Applicant: TOPCON CORPORATION, Tokyo (JP)

(72) Inventors: Ryoichi Hirose, Itabashi-ku (JP); Tatsuo Yamaguchi, Warabi (JP)

(73) Assignee: TOPCON CORPORATION, Tokyo (JP)

( * ) Notice: Subject to any disclaimer, the term of this patent is extended or adjusted under 35 U.S.C. 154(b) by 245 days.

(21) Appl. No.: 16/718,223

(22) Filed: Dec. 18, 2019

(65) Prior Publication Data
US 2020/0205659 A1 Jul. 2, 2020

(30) Foreign Application Priority Data
Dec. 26, 2018 (JP) .............................. JP2018-242944

(51) Int. Cl.
| A61B 3/15 | (2006.01) |
| A61B 3/00 | (2006.01) |
| A61B 3/10 | (2006.01) |
| A61B 3/103 | (2006.01) |
| A61B 3/12 | (2006.01) |

(52) U.S. Cl.
CPC ............ *A61B 3/152* (2013.01); *A61B 3/0025* (2013.01); *A61B 3/102* (2013.01); *A61B 3/103* (2013.01); *A61B 3/1025* (2013.01); *A61B 3/12* (2013.01)

(58) Field of Classification Search
CPC ....... A61B 3/152; A61B 3/0025; A61B 3/102; A61B 3/1025; A61B 3/103; A61B 3/12
USPC ......................................................... 351/208
See application file for complete search history.

(56) References Cited

U.S. PATENT DOCUMENTS

| 2005/0219545 | A1 | 10/2005 | Chan et al. |
| 2012/0002164 | A1 | 1/2012 | Yamamoto et al. |
| 2013/0188129 | A1* | 7/2013 | Inoue ................. A61B 3/102 351/206 |
| 2014/0192323 | A1 | 7/2014 | Kakuma |
| 2016/0038023 | A1* | 2/2016 | Endo ................. A61B 3/102 351/206 |
| 2016/0051137 | A1* | 2/2016 | Vestri ................ A61B 3/107 351/206 |

FOREIGN PATENT DOCUMENTS

| EP | 1 582 142 A1 | 10/2005 |
| EP | 2 404 545 A2 | 1/2012 |
| EP | 2 692 274 A1 | 2/2014 |
| JP | 2011-170209 A | 9/2011 |

OTHER PUBLICATIONS

Extended European Search Report dated Apr. 28, 2020 in European Patent Application No. 19213727.1, 7 pages.

* cited by examiner

*Primary Examiner* — Mohammed A Hasan
(74) *Attorney, Agent, or Firm* — Xsensus LLP

(57) ABSTRACT

An ophthalmologic apparatus includes an acquisition unit and a controller. The acquisition unit includes an optical scanner capable of deflecting light in a predetermined deflection angle range. The acquisition unit is configured to acquire data of a subject's eye by performing A-scan on the subject's eye using optical coherence tomography by measurement light deflected by the optical scanner. The controller is configured to cause the acquisition unit to perform A-scan based on a deflection operation state of the optical scanner.

16 Claims, 9 Drawing Sheets

OPHTHALMOLOGIC APPARATUS AND METHOD FOR CONTROLLING THE SAME

CROSS-REFERENCE TO RELATED APPLICATION

This application is based upon and claims the benefit of priority from Japanese Patent Application No. 2018-242944, filed Dec. 26, 2018; the entire contents of which are incorporated herein by reference.

FIELD

Embodiments according to present invention described herein relate to an ophthalmologic apparatus and a method of controlling the same.

BACKGROUND

In recent years, attention has been drawn to optical coherence tomography (OCT) which is used to measure the morphology of an object to be measured or to image using light beam emitted from a laser light source or the like. Since OCT does not have invasiveness to human body as X-ray CT (Computed Tomography) does, development of application of OCT in medical field and biology field is particularly expected. For example, in the ophthalmologic field, apparatuses for forming images of the fundus or the cornea have been in practical use. Such apparatuses using OCT (OCT apparatuses) can be used to observe a variety of sites (a fundus, or an anterior segment) of a subject's eye. In addition, because of the ability to acquire high precision images, the OCT apparatuses are applied to the diagnosis of various eye diseases.

In the measurement (imaging) using OCT, scan is performed on the measurement site using measurement light deflected by an optical scanner. For example, in Japanese Unexamined Patent Application Publication No. 2011-170209, a technique for ensuring the linearity of a scanning trajectory by constantly performing correction calculation on a movement command value of a galvano scanner.

SUMMARY

One aspect of some embodiments is an ophthalmologic apparatus including: an acquisition unit including an optical scanner capable of deflecting light in a predetermined deflection angle range and configured to acquire data of a subject's eye by performing A-scan on the subject's eye using optical coherence tomography by measurement light deflected by the optical scanner; and a controller configured to cause the acquisition unit to perform A-scan based on a deflection operation state of the optical scanner.

Another aspect of some embodiments is a method of controlling an ophthalmologic apparatus including an optical scanner capable of deflecting light in a predetermined deflection angle range. The method of controlling the ophthalmologic apparatus includes: an acquisition step of acquiring data of a subject's eye by performing A-scan on the subject's eye using optical coherence tomography by measurement light deflected by the optical scanner; and a control step of performing A-scan based on a deflection operation state of the optical scanner.

DETAILED DESCRIPTION

Figure 1:
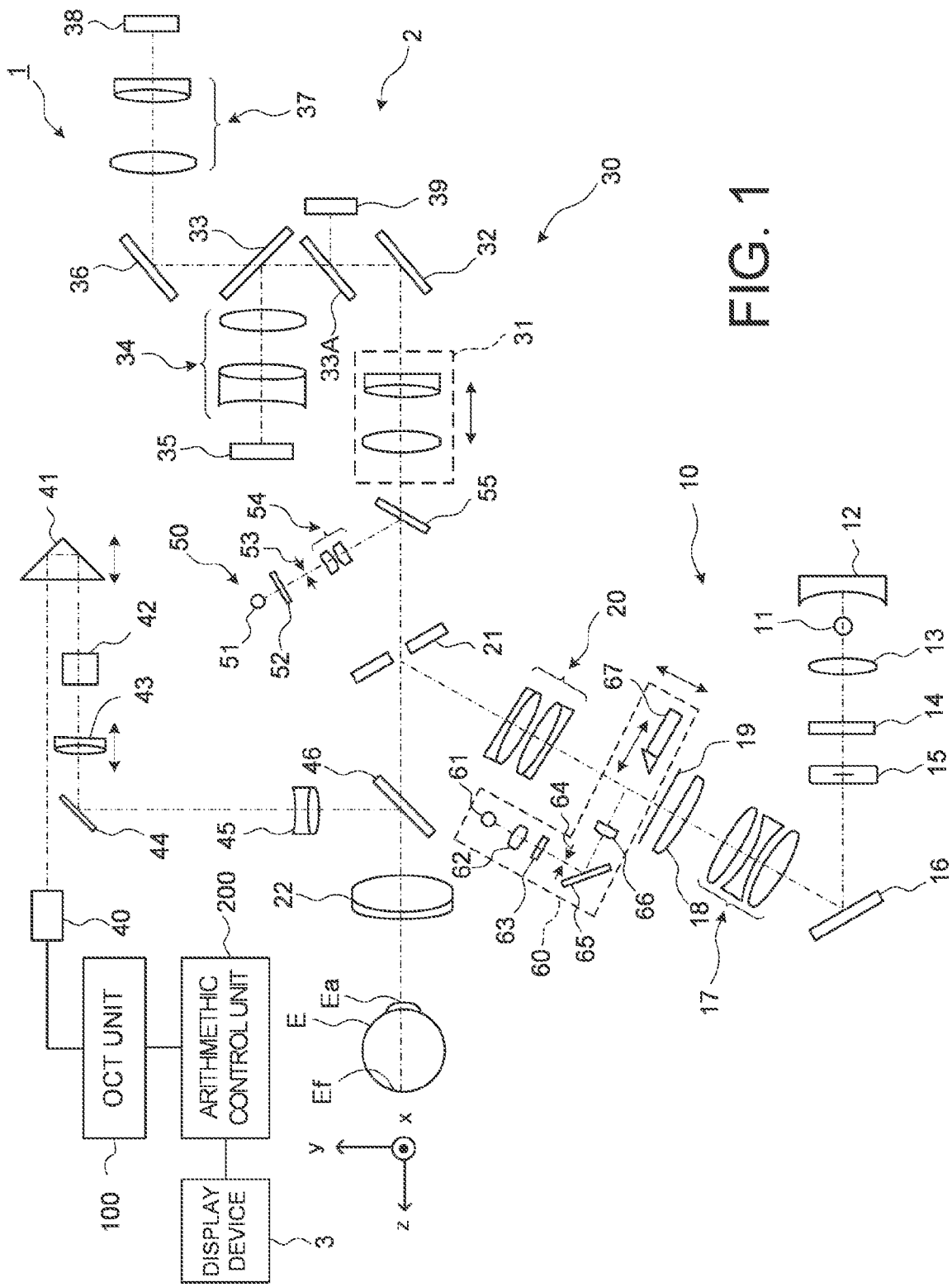
FIG. 1 is a schematic diagram illustrating an example of the configuration of an ophthalmologic apparatus according to embodiments.

In a measuring using OCT, acquiring a measurement result with a wider angle and higher definition is demanded. Therefore, optical scanners are required to operate at a higher speed in a wider deflection angle range. However, the optical scanners such as a galvano scanner are difficult to follow high-speed operation.

Thus, the acquisition of a desired measurement result in OCT measurement is limited by the operating characteristics of the optical scanner.

According to some embodiments of the present invention, a new technique for performing OCT measuring using an optical scanner can be provided.

Referring now to the drawings, exemplary embodiments of an ophthalmologic apparatus and a method of controlling the ophthalmologic apparatus according to the present invention are described below. Any of the contents of the documents cited in the present specification and arbitrary known techniques may be applied to the embodiments below.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

An ophthalmologic apparatus according to the embodiments includes an optical scanner capable of deflecting light in a predetermined deflection angle range. The ophthalmologic apparatus can perform OCT on the subject's eye using measurement light deflected in a predetermined deflection direction by the optical scanner. At this time, the ophthalmologic apparatus performs OCT measurement (at least A-scan) at a timing corresponding to a deflection operation state of the optical scanner. Examples of the deflection operation state of the optical scanner include a deflection angle of a mirror (deflection member) deflecting the measurement light (deflection angle of the optical scanner), a deflection frequency of the mirror (deflection speed, deflection cycle), or the like. The deflection angle of the mirror can be specified from the deflection frequency set in advance for the mirror set at a predetermined deflection angle, for example.

Thereby, a data set group in an A-scan direction in consideration of an operating characteristics of the optical scanner can be acquired. For example, without being affected by the non-linear operation of the optical scanner, a data set group at scan positions scanned at substantially equal scan angles (deflection angle) or substantially equal scan intervals. Here, the non-linear operation of the optical scanner means an operation in which the deflection angles of the optical scanner does not change linearly with respect to changes in time (A-scan execution timings, data acquiring timings).

Hereinafter, in the embodiments, the case of using the swept source type OCT method in the measurement or the imaging (photographing) using OCT will be described. However, the configuration according to the embodiments can also be applied to an ophthalmologic apparatus using other type of OCT (for example, spectral domain type OCT).

Hereinafter, the case in which the optical scanner includes a galvano scanner will be described. However, the following embodiments can also be applied when the optical scanner includes a deflection member other than the galvano scanner. Further, hereinafter, a deflection angle versus time characteristics will be described as an example of the operating characteristics of the optical scanner. However, the following embodiments can be applied to other operating characteristics of the optical scanner.

In this specification, images acquired using OCT may be collectively referred to as "OCT images". Also, the measurement operation for forming OCT images may be referred to as OCT measurement.

The ophthalmologic apparatus according to some embodiments includes any one or more of an ophthalmologic imaging apparatus, an ophthalmologic measuring apparatus, and an ophthalmologic therapy apparatus. The ophthalmologic imaging apparatus included in the ophthalmologic apparatus according to some embodiments includes, for example, any one or more of a fundus camera, a scanning laser ophthalmoscope, a slit lamp ophthalmoscope, a surgical microscope, and the like. Further, the ophthalmologic measuring apparatus included in the ophthalmologic apparatus according to some embodiments includes any one or more of an eye refractivity examination apparatus, a tonometer, a specular microscope, a wave-front analyzer, a perimeter, a microperimeter, and the like, for example. Further, the ophthalmologic therapy apparatus included in the ophthalmologic apparatus according to some embodiments includes any one or more of a laser therapy apparatus, a surgical apparatus, a surgical microscope, and the like, for example.

The ophthalmologic apparatus according to the following embodiments includes an OCT apparatus and a fundus camera. The OCT apparatus can perform OCT measurement. Alternatively, the configuration according to the following embodiments may be applied to a single-functional OCT apparatus.

Hereinafter, an ophthalmologic apparatus capable of performing OCT measurement on a fundus of the subject's eye will be mainly described as an example. However, the ophthalmologic apparatus according to the embodiments may be capable of performing OCT measurement on an anterior segment of the subject's eye. In some embodiments, a measurement site of the OCT measurement and/or a range of the OCT measurement are changed by moving a lens for changing focal position of the measurement light. In some embodiments, the ophthalmologic apparatus has a configuration capable of performing OCT measurement on the fundus, OCT measurement on the anterior segment, and OCT measurement on the whole eyeball including the fundus and anterior segment, by adding one or more attachments (objective lens, front lens, etc.). In some embodiments, in the ophthalmologic apparatus for measuring fundus, OCT measurement is performed on the anterior segment, by making the measurement light incident on the subject's eye, the measurement light having been converted into a parallel light flux by arranging a front lens between the objective lens and the subject's eye.

First Embodiment

The ophthalmologic apparatus according to a first embodiment performs OCT measurement under feed-forward control on the subject's eye.

Configuration

Optical System

As shown in FIG. 1, the ophthalmologic apparatus 1 includes a fundus camera unit 2, an OCT unit 100, and an arithmetic control unit 200. The fundus camera unit 2 is provided with an optical system and a mechanism for acquiring front images of a subject's eye E. The OCT unit 100 is provided with a part of an optical system and a mechanism for performing OCT. Another part of the optical system and the mechanism for performing OCT are provided in the fundus camera unit 2. The arithmetic control unit 200 includes one or more processors for performing various kinds of arithmetic processing and control processing. In addition to these elements, an arbitrary element or a unit, such as a member (chin rest, forehead pad, etc.) for supporting a face of the subject, a lens unit (for example, an attachment for an anterior segment OCT) for switching the target site of OCT, and the like, may be provided in the ophthalmologic apparatus 1. In some embodiments, the lens unit is configured to be manually inserted and removed between the subject's eye E and an objective lens 22 described later. In some embodiments, the lens unit is configured to be automatically inserted and removed between the subject's eye E and an objective lens 22 described later, under the control of the arithmetic control unit 200 (controller 210 described later).

The term "processor" as used herein refers to a circuit such as, for example, a central processing unit (CPU), a graphics processing unit (GPU), an application specific integrated circuit (ASIC), and a programmable logic device (PLD). Examples of PLD include a simple programmable logic device (SPLD), a complex programmable logic device (CPLD), and a field programmable gate array (FPGA). The processor realizes, for example, the function according to the embodiments by reading out a computer program stored in a storage circuit or a storage device and executing the computer program.

Fundus Camera Unit

The fundus camera unit 2 is provided with an optical system for imaging (photographing) a fundus Ef of the subject's eye E. An image (called fundus image, fundus photograph, etc.) of the fundus Ef to be obtained is a front image such as an observation image, a photographic image, or the like. The observation image is obtained by moving image shooting using near infrared light. The photographic image is a still image using flash light. Furthermore, the fundus camera unit 2 can obtain the front image (anterior segment image) by photographing (imaging) an anterior segment Ea of the subject's eye E.

The fundus camera unit 2 includes an illumination optical system 10 and an imaging optical system 30. The illumination optical system 10 projects illumination light onto the subject's eye E. The imaging optical system 30 detects returning light of the illumination light from the subject's eye E. Measurement light from the OCT unit 100 is guided to the subject's eye E through an optical path in the fundus camera unit 2. Returning light of the measurement light is guided to the OCT unit 100 through the same optical path.

Light (observation illumination light) emitted from the observation light source 11 of the illumination optical system 10 is reflected by a reflective mirror 12 having a curved reflective surface, and becomes near-infrared light after penetrating a visible cut filter 14 via a condenser lens 13. Further, the observation illumination light is once converged near an imaging light source 15, is reflected by a mirror 16, and passes through relay lenses 17 and 18, a diaphragm 19, and a relay lens 20. Then, the observation illumination light is reflected on the peripheral part (the surrounding area of a hole part) of a perforated mirror 21, penetrates a dichroic mirror 46, and is refracted by an objective lens 22, thereby illuminating the subject's eye E (fundus Ef or anterior segment Ea). Returning light of the observation illumination light reflected from the subject's eye E is refracted by the objective lens 22, penetrates the dichroic mirror 46, passes through the hole part formed in the center area of the perforated mirror 21, penetrates a dichroic mirror 55. The returning light penetrating the dichroic mirror 55 travels through a photography focusing lens 31 and is reflected by a mirror 32. Further, this returning light penetrates a half mirror 33A, is reflected by a dichroic mirror 33, and forms an image on the light receiving surface of an image sensor 35 by a condenser lens 34. The image sensor 35 detects the returning light at a predetermined frame rate. It should be noted that the focus of the imaging optical system 30 is adjusted so as to coincide with the fundus Ef or the anterior segment Ea.

Light (imaging illumination light) output from the imaging light source 15 is projected onto the fundus Ef via the same route as that of the observation illumination light. Returning light of the imaging illumination light from the subject's eye E is guided to the dichroic mirror 33 via the same route as that of the observation illumination light, penetrates the dichroic mirror 33, is reflected by a mirror 36, and forms an image on the light receiving surface of the image sensor 38 by a condenser lens 37.

A liquid crystal display (LCD) 39 displays a fixation target and a visual target used for visual acuity measurement. Part of light output from the LCD 39 is reflected by the half mirror 33A, is reflected by the mirror 32, travels through the photography focusing lens 31 and the dichroic mirror 55, and passes through the hole part of the perforated mirror 21. The light flux (beam) having passed through the hole part of the perforated mirror 21 penetrates the dichroic mirror 46, and is refracted by the objective lens 22, thereby being projected onto the fundus Ef.

By changing the display position of the fixation target on the screen of the LCD 39, the fixation position of the subject's eye E can be changed. Examples of the fixation position include a fixation position for acquiring an image centered at a macula, a fixation position for acquiring an image centered at an optic disc, a fixation position for acquiring an image centered at a fundus center between the macula and the optic disc, a fixation position for acquiring an image of a site (fundus peripheral part) far away from the macula, and the like. The ophthalmologic apparatus 1 according to some embodiments includes GUI (Graphical User Interface) and the like for designating at least one of such fixation positions. The ophthalmologic apparatus 1 according to some embodiments includes GUI etc. for manually moving the fixation position (display position of the fixation target).

The configuration for presenting the movable fixation target to the subject's eye E is not limited to the display device such LCD or the like. For example, the movable fixation target can be generated by selectively turning on a plurality of light sources of a light source array (light emitting diode (LED) array or the like). Alternatively, the movable fixation target can be generated using one or more movable light sources.

Further, the ophthalmologic apparatus 1 may be provided with one or more external fixation light sources. One of the one or more external fixation light sources can project fixation light onto a fellow eye of the subject's eye E. A projection position of the fixation light on the fellow eye can be changed. By changing the projection position of the fixation light on the fellow eye, the fixation position of the subject's eye E can be changed. The projection position by the external fixation light source(s) may be the same as the projection position of the subject's eye E using the LCD 39. For example, the movable fixation target can be generated by selectively turning on a plurality of external fixation light sources. Alternatively, the movable fixation target can be generated using one or more movable external fixation light sources.

The alignment optical system 50 generates an alignment indicator for alignment of the optical system with respect to the subject's eye E. Alignment light output from an LED 51 travels through the diaphragms 52 and 53 and the relay lens 54, is reflected by the dichroic mirror 55, and passes through the hole part of the perforated mirror 21. The alignment light having passed through the hole part of the perforated mirror 21 penetrates the dichroic mirror 46, and is projected onto the subject's eye E by the objective lens 22. Corneal reflection light of the alignment light is guided to the image sensor 35 through the same route as the returning light of the observation illumination light. Manual alignment or automatic alignment can be performed based on the received light image (alignment indicator image) thereof.

The focus optical system 60 generates a split indicator for adjusting the focus with respect to the subject's eye E. The focus optical system 60 is movable along an optical path (illumination optical path) of the illumination optical system 10 in conjunction with the movement of the photography focusing lens 31 along an optical path (imaging optical path) of the imaging optical system 30. The reflection rod 67 can be inserted and removed into and from the illumination optical path. To conduct focus adjustment, the reflective surface of the reflection rod 67 is arranged in a slanted position on the illumination optical path. Focus light output from an LED 61 passes through a relay lens 62, is split into two light beams by a split indicator plate 63, passes through a two-hole diaphragm 64, is reflected by a mirror 65, and is reflected after an image is once formed on the reflective surface of the reflection rod 67 by a condenser lens 66.

Further, the focus light travels through the relay lens 20, is reflected by the perforated mirror 21, penetrates the dichroic mirror 46, and is refracted by the objective lens 22, thereby being projected onto the fundus Ef. Fundus reflection light of the focus light is guided to the image sensor 35 through the same route as the corneal reflection light of the alignment light. Manual focus or automatic focus can be performed based on the received light image (split indicator image) thereof The dichroic mirror 46 combines an optical path for fundus photography and an optical path for OCT. The dichroic mirror 46 reflects light of wavelength band used in OCT, and transmits light for fundus photography. The optical path for OCT (optical path of measurement light) is provided with, in order from the OCT unit 100 side to the dichroic mirror 46 side, a collimator lens unit 40, an optical path length changing unit 41, an optical scanner 42, an OCT focusing lens 43, a mirror 44, and a relay lens 45.

The optical path length changing unit 41 is movable in directions indicated by the arrow in FIG. 1, thereby changing the length of the optical path for OCT. This change in the optical path length is used for correcting the optical path length according to the axial length, adjusting the interference state, or the like. The optical path length changing unit 41 includes a corner cube and a mechanism for moving the corner cube.

The optical scanner 42 is disposed at a position optically conjugate with the pupil of the subject's eye E. The optical scanner 42 deflects the measurement light LS traveling along the OCT optical path. The optical scanner 42 can deflect the measurement light LS in a one-dimensionally or two-dimensional manner.

In case that the optical scanner deflects the measurement light LS in a one-dimensionally manner, the optical scanner 42 includes a galvano scanner capable of deflecting the measurement light LS within a predetermined deflection angle range in a predetermined deflection direction. In case that the optical scanner deflects the measurement light LS in a two-dimensionally manner, the optical scanner 42 includes a first galvano scanner and a second galvano scanner. The first galvano scanner deflects the measurement light LS so as to scan a photographing (imaging) site (fundus Ef or the anterior segment) in a horizontal direction orthogonal to the optical axis of the OCT optical system 8. The second galvano scanner deflects the measurement light LS deflected by the first galvano mirror so as to scan the photographing site in a vertical direction orthogonal to the optical axis of the OCT optical system 8. Examples of scan mode with the measurement light LS performed by the optical scanner 42 include a horizontal scan, a vertical scan, a cross scan, a radial scan, a circle scan, a concentric scan, a helical (spiral) scan, and the like.

The optical scanner 42 is configured to be controllable by the arithmetic control unit 200 (controller 210). In some embodiments, the optical scanner 42 is configured such that at least one of the deflection angle range and the deflection frequency (deflection speed, deflection cycle) can be set by the arithmetic control unit 200 (controller 210). In some embodiments, the optical scanner 42 is configured such that information defining the control waveform for controlling the deflection operation can be set by the arithmetic control unit 200 (controller 210). The control waveform defines the deflection angle range and the deflection frequency. The optical scanner performs deflection operation in accordance with the set control waveform. The arithmetic control unit 200 (controller 210) can operate each of the first galvano scanner and the second galvano scanner in a desired deflection angle range or at a desired deflection frequency.

In some embodiments, the optical scanner 42 outputs operation information including an operation state of the optical scanner 42 under the control of the arithmetic control unit 200 (controller 210). The operation information includes information representing a deflection angle (for example, a current value or a voltage value corresponding to the deflection angle). In some embodiments, the optical scanner 42 includes a mirror that deflects the measurement light and a driver that drives the mirror. The operation information includes information representing the deflection angle of the mirror. The arithmetic control unit 200 (controller 210) can monitor the operation state of each of the first galvano scanner and the second galvano scanner.

The OCT focusing lens 43 is moved along the optical path of the measurement light LS in order to perform focus adjustment of the optical system for OCT. The OCT focusing lens 43 can move within a moving range. The moving range includes a first lens position for placing the focal position of the measurement light LS at the fundus Ef or near the fundus Ef of the subject's eye E and a second lens position for making the measurement light LS projected onto the subject's eye E a parallel light beam. The movement of the photography focusing lens 31, the movement of the focus optical system 60, and the movement of the OCT focusing lens 43 can be controlled in conjunction with each other.

OCT Unit

Figure 2:
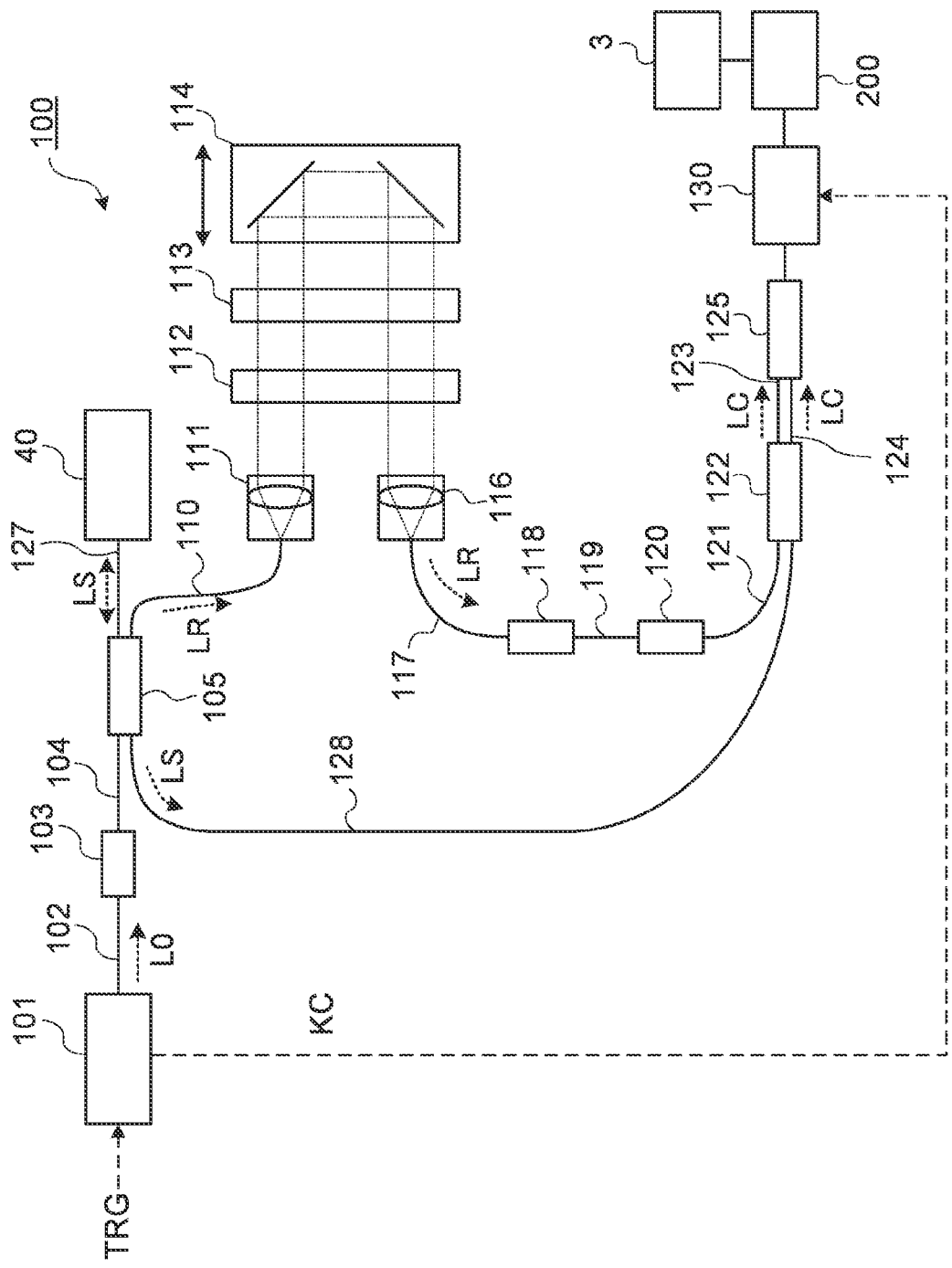
FIG. 2 is a schematic diagram illustrating an example of the configuration of an ophthalmologic apparatus according to the embodiments.

An example of the configuration of the OCT unit 100 is shown in FIG. 2. The OCT unit 100 is provided with an optical system for acquiring OCT images of the subject's eye E. The optical system includes an interference optical system that splits light from a wavelength sweeping type (i.e., a wavelength scanning type) light source into measurement light and reference light, makes the measurement light returning from the subject's eye E and the reference light having traveled through the reference optical path interfere with each other to generate interference light, and detects the interference light. The detection result of the interference light obtained by the interference optical system (i.e., the detection signal) is an interference signal indicating the spectrum of the interference light, and is sent to the arithmetic control unit 200.

Like swept source type ophthalmologic apparatuses commonly used, the light source unit 101 includes a wavelength sweeping type (i.e., a wavelength scanning type) light source capable of sweeping (scanning) the wavelengths of emitted light. The wavelength sweeping type light source includes a laser light source that includes a resonator. The light source unit 101 temporally changes the output wavelengths within the near-infrared wavelength bands that cannot be visually recognized with human eyes.

The light source unit 101 can receive the control signal TRG from the arithmetic control unit 200 (controller 210) and can start the wavelength sweep operation described above. Thereby, the arithmetic control unit 200 (controller 210) can control the execution timing of the A-scan using the control signal TRG.

Light L0 output from the light source unit 101 upon receiving the control signal TRG from the arithmetic control unit 200 (controller 210) is guided to the polarization controller 103 through the optical fiber 102, and the polarization state of the light L0 is adjusted. The polarization controller 103, for example, applies external stress to the looped optical fiber 102 to thereby adjust the polarization state of the light L0 guided through the optical fiber 102.

The light L0 whose polarization state has been adjusted by the polarization controller 103 is guided to the fiber coupler 105 through the optical fiber 104, and is split into the measurement light LS and the reference light LR.

The reference light LR is guided to the collimator 111 through the optical fiber 110. The reference light LR is converted into a parallel light beam by the collimator 111. Then, the reference light LR is guided to the optical path length changing unit 114 via an optical path length correction member 112 and a dispersion compensation member 113. The optical path length correction member 112 acts so as to match the optical path length of the reference light LR with the optical path length of the measurement light LS. The dispersion compensation member 113 acts so as to match the dispersion characteristics between the reference light LR and the measurement light LS.

The optical path length changing unit 114 is movable in directions indicated by the arrow in FIG. 2, thereby changing the length of the optical path of the reference light LR. Through such movement, the length of the optical path of the reference light LR is changed. The change in the optical path length is used for the correction of the optical path length according to the axial length of the subject's eye E, for the adjustment of the interference state, or the like. The optical path length changing unit 114 includes, for example, a corner cube and a movement mechanism for moving the corner cube. In this case, the corner cube in the optical path length changing unit 114 changes the traveling direction of the reference light LR that has been made into the parallel light flux by the collimator 111 in the opposite direction. The optical path of the reference light LR incident on the corner cube and the optical path of the reference light LR emitted from the corner cube are parallel.

The reference light LR that has traveled through the optical path length changing unit 114 passes through the dispersion compensation member 113 and the optical path length correction member 112, is converted from the parallel light beam to the convergent light beam by a collimator 116, and enters an optical fiber 117. The reference light LR that has entered the optical fiber 117 is guided to a polarization controller 118, and the polarization state of the reference light LR is adjusted. Then the reference light LR is guided to an attenuator 120 through an optical fiber 119, and the light amount of the reference light LR is adjusted. After that, the reference light LR is guided to a fiber coupler 122 through an optical fiber 121.

The configuration shown in FIG. 1 and FIG. 2 includes both the optical path length changing unit 41 that changes the length of the optical path of the measurement light LS (i.e., measurement optical path or measurement arm) and the optical path length changing unit 114 that changes the length of the optical path of the reference light LR (i.e., reference optical path or reference arm). However, any one of the optical path length changing units 41 and 114 may be provided. The difference between the measurement optical path length and the reference optical path length can be changed by using other optical members.

Meanwhile, the measurement light LS generated by the fiber coupler 105 is guided through the optical fiber 127, and is made into the parallel light beam by the collimator lens unit 40. The measurement light LS made into the parallel light flux is guided to the dichroic mirror 46 via the optical path length changing unit 41, the optical scanner 42, the OCT focusing lens 43, the mirror 44, and the relay lens 45. The measurement light LS guided to the dichroic mirror 46 is reflected by the dichroic mirror 46, refracted by the objective lens 22, and projected onto the subject's eye E. The measurement light LS is scattered (and reflected) at various depth positions of the subject's eye E. The returning light of the measurement light LS including such backscattered light advances through the same path as the outward path in the opposite direction and is led to the fiber coupler 105, and then reaches the fiber coupler 122 through the optical fiber 128.

The fiber coupler 122 combines (interferes) the measurement light LS incident through the optical fiber 128 and the reference light LR incident through the optical fiber 121 to generate interference light. The fiber coupler 122 generates a pair of interference light LC by splitting the interference light generated from the measurement light LS and the reference light LR at a predetermined splitting ratio (for example, 1:1). The pair of the interference light LC emitted from the fiber coupler 122 is guided to the detector 125 through the optical fibers 123 and 124, respectively.

The detector 125 is, for example, a balanced photodiode that includes a pair of photodetectors for respectively detecting the pair of interference light LC and outputs the difference between the pair of detection results obtained by the pair of photodetectors. The detector 125 sends the detection result (i.e., interference signal) to the data acquisition system (DAQ) 130. A clock KC is supplied from the light source unit 101 to the DAQ 130. The clock KC is generated in the light source unit 101 in synchronization with the output timing of each wavelength sweeping (scanning) within a predetermined wavelength range performed by the wavelength sweeping type light source. For example, the light source unit 101 optically delays one of the two pieces of branched light obtained by branching the light L0 of each output wavelength, and then generates the clock KC based on the result of the detection of the combined light of the two pieces of branched light. The DAQ 130 performs the sampling of the detection result obtained by the detector 125 based on the clock KC. The DAQ 130 sends the result of the sampling of the detection result obtained by the detector 125 to the arithmetic control unit 200. For example, the arithmetic control unit 200 performs the Fourier transform etc. on the spectral distribution based on the detection result obtained by the detector 125 for each series of wavelength scanning (i.e., for each A line). With this, the reflection intensity profile for each A line is formed. In addition, the arithmetic control unit 200 forms image data by applying imaging processing to the reflection intensity profiles for the respective A lines.

Arithmetic Control Unit

The arithmetic control unit 200 analyzes the detection signals fed from the DAQ 130 to form an OCT image of the fundus Ef. The arithmetic processing for the OCT image formation is performed in the same manner as in the conventional swept-source-type OCT apparatus.

In addition, the arithmetic control unit 200 controls each part of the fundus camera unit 2, the display device 3, and the OCT unit 100.

Also, as the control of the fundus camera unit 2, the arithmetic control unit 200 performs following controls: the operation control of the observation light source 11, of the imaging light source 15 and of the LEDs 51 and 61; the operation control of the LCD 39; the movement control of the photography focusing lens 31; the movement control of the OCT focusing lens 43; the movement control of the reflection rod 67; the movement control of the focus optical system 60; the movement control of the optical path length changing unit 41; the operation control of the optical scanner 42, and the like.

For example, the arithmetic control unit 200 controls the display device 3 to display the OCT image of the subject's eye E.

Further, as the control of the OCT unit 100, the arithmetic control unit 200 controls: the operation of the light source unit 101; the operation of the optical path length changing unit 114; the operations of the attenuator 120; the operation of the polarization controllers 103 and 118; the operation of the detector 125; the operation of the DAQ 130; and the like.

As in the conventional computer, the arithmetic control unit 200 includes a microprocessor, RAM, ROM, hard disk drive, and communication interface, for example. A storage device such as the hard disk drive stores a computer program for controlling the ophthalmologic apparatus 1. The arithmetic control unit 200 may include various kinds of circuitry such as a circuit board for forming OCT images. In addition, the arithmetic control unit 200 may include an operation device (or an input device) such as a keyboard and a mouse, and a display device such as an LCD.

The fundus camera unit 2, the display device 3, the OCT unit 100, and the arithmetic control unit 200 may be integrally provided (i.e., in a single housing), or they may be separately provided in two or more housings.

Control System

Figure 3:
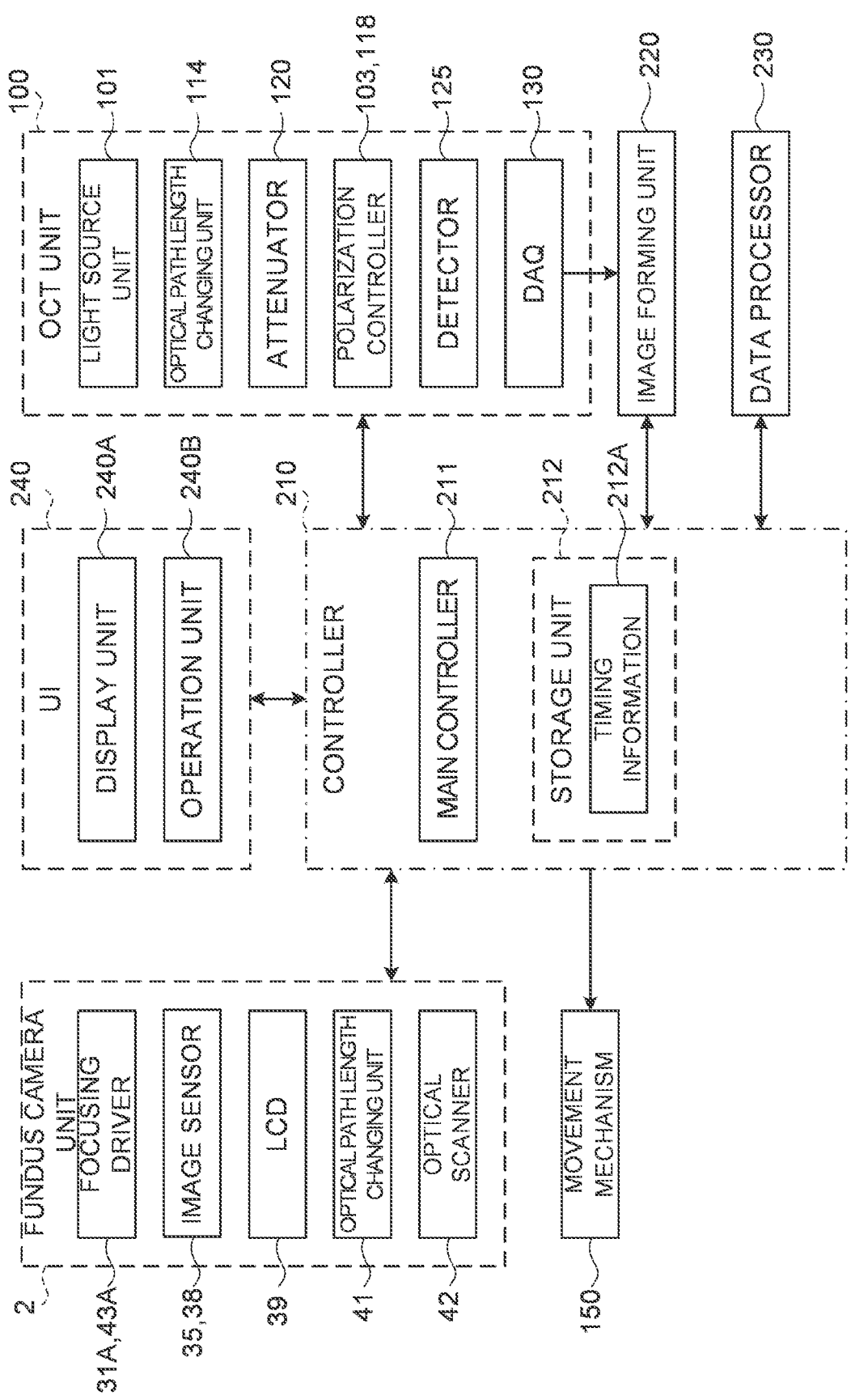
FIG. 3 is a schematic block diagram illustrating an example of the configuration of the ophthalmologic apparatus according to the embodiments.

The arithmetic control unit 200 includes the controller 210, an image forming unit 220, and a data processor 230, as shown in FIG. 3. The functions of the arithmetic control unit 200 is realized by one or more processors. In some embodiments, the function of the arithmetic control unit 200 is realized by a control processor that realizes the function of the controller 210, an image forming processor that realizes the function of the image forming unit 220, and a data processing processor that realizes the function of the data processor 230.

FIG. 3 illustrates a configuration example of a control system of the ophthalmologic apparatus 1. In FIG. 3, a part of the components included in the ophthalmologic apparatus 1 is omitted.

Controller

The controller 210 executes various controls. The controller 210 includes a main controller 211 and a storage unit 212.

Main Controller

The main controller 211 includes a processor and controls each part of the ophthalmologic apparatus 1. For example, the main controller 211 controls components of the fundus camera unit 2 such as focusing drivers 31A and 43A, the image sensors 35 and 38, the LCD 39, the optical path length changing unit 41, the optical scanner 42, and the entire optical system (movement mechanism 150). Further, the main controller 211 controls components of the OCT unit 100 such as the light source unit 101, the optical path length changing unit 114, the attenuator 120, the polarization controllers 103 and 118, the detector 125, and the DAQ 130.

For example, the main controller 211 controls the LCD 39 to display the fixation target at a position on the screen of the LCD 39 corresponding the fixation position set manually or automatically. Moreover, the main controller 211 can change the display position of the fixation target displayed on the LCD 39 (in a continuous manner or in a phased manner). Thereby, the fixation target can be moved (that is, the fixation position can be changed). The display position of the fixation target and movement mode of the fixation target are set manually or automatically. Manual setting is performed using GUI, for example. Automatic setting is performed by the data processor 230, for example.

The focusing driver 31A moves the photography focusing lens 31 in the direction along the optical axis of the imaging optical system 30, and moves the focus optical system 60 in the direction along the optical axis of the illumination optical system 10. With this, the focus position of the imaging optical system 30 is changed. The focusing driver 31A may include a dedicated mechanism for moving the photography focusing lens 31 and a dedicated mechanism for moving the focus optical system 60. The focusing driver 31A is controlled when focus adjustment etc. is performed.

The focusing driver 43A moves the OCT focusing lens 43 in the optical axis direction of the measurement optical path. As a result, the focus position of the measurement light LS is changed. For example, the focus position of the measurement light LS can be arranged at the fundus Ef or near the fundus Ef by moving the OCT focusing lens 43 to the first lens position. For example, the focus position of the measurement light LS can be arranged at a far point position by moving the OCT focusing lens 43 to the second lens position. The focus position of the measurement light LS corresponds to the depth position (z position) of the beam waist of the measurement light LS.

The movement mechanism 150 three-dimensionally moves at least the fundus camera unit 2 (optical system), for example. In a typical example, the movement mechanism 150 includes a mechanism for moving at least the fundus camera unit 2 in the x direction (left-right direction, horizontal direction), a mechanism for moving it in the y direction (up-down direction, vertical direction), and a mechanism for moving it in the z direction (depth direction, front-back direction). The mechanism for moving in the x direction includes a x stage movable in the x direction and a x movement mechanism for moving the x stage, for example. The mechanism for moving in the y direction includes a y stage movable in the y direction and a y movement mechanism for moving the y stage, for example. The mechanism for moving in the z direction includes a z stage movable in the z direction and a z movement mechanism for moving the z stage, for example. Each movement mechanism includes an actuator such as a pulse motor, and operates under the control of the main controller 211.

The control for the movement mechanism 150 is used for alignment and tracking. Here, tracking is to move the optical system of the apparatus according to the movement of the subject's eye E. To perform tracking, alignment and focus adjustment are performed in advance. The tracking is a function of maintaining a suitable positional relationship in which alignment and focusing are matched by causing the position of the optical system of the apparatus and the like to follow the eye movement. In some embodiments, the movement mechanism 150 is configured to be controlled to change the optical path length of the reference light (that is, the difference of the optical path length between the optical path of the measurement light and the optical path of the reference light).

In the case of manual alignment, a user operates a user interface (UI) 240 described later to relatively move the optical system and subject's eye E so as to cancel the displacement of the subject's eye E with respect to the optical system. For example, the main controller 211 controls the movement mechanism 150 to relatively move the optical system and the subject's eye E by outputting a control signal corresponding to the operation content with respect to the user interface 240 to the movement mechanism 150.

In the case of automatic alignment, the main controller 211 controls the movement mechanism 150 to relatively move the optical system and the subject's eye E so as to cancel the displacement of the subject's eye E with respect to the optical system. In some embodiments, the main controller 211 controls the movement mechanism 150 to relatively move the optical system and the subject's eye E by outputting a control signal to the movement mechanism 150 so that the optical axis of the optical system substantially coincides with the axis of the subject's eye E and the distance of the optical system with respect to the subject's eye E is a predetermined working distance. Here, the working distance is a preset value which is called a working distance of the objective lens 22, and it means the distance between the subject's eye E and the optical system when measuring (imaging) using the optical system.

The main controller 211 controls the fundus camera unit 2 etc. to control the fundus imaging (photography) and the anterior segment imaging. Further, the main controller 211 controls the fundus camera unit 2 and the OCT unit 100 etc. to control the OCT measurement. The main controller 211 is capable of performing a plurality of preliminary operations prior to OCT measurement. Examples of the preliminary operation include alignment, rough focus adjustment, polarization adjustment, and fine focus adjustment. The plurality of preliminary operations is performed in a predetermined order. In some embodiments, the plurality of preliminary operations is performed in an order described above.

It should be noted that the types and the orders of the preliminary operations are not so limited, and they may be optional. For example, the preliminary operations may further include small-pupil judgment. The small-pupil judgment is a preliminary operation to judge whether the pupil of the subject's eye E is small or not (whether the subject's eye E is microcoria or not). The small-pupil judgment may be performed between the rough focus adjustment and the optical path length difference adjustment. In some embodiments, the small-pupil judgment includes, for example, a series of processes as follows: acquiring a front image (anterior segment image) of the subject's eye E; specifying an image region corresponding to the pupil; calculating the size (e.g., diameter, circumference length) of the pupil region; judging whether the pupil of the subject's eye E is small or not based on the calculated size (threshold processing); and controlling the diaphragm 19 when judged that the pupil of the subject's eye E is small. In some embodiments, the calculation of the size of the pupil area includes processing of circularly or elliptically approximating the pupil region.

The rough focus adjustment is a kind of focus adjustment using the split indicator. The rough focus adjustment may be performed by determining the position of the photography focusing lens 31 based on information, which is obtained by associating the eye refractive power acquired in advance with the position of the photography focusing lens 31, and a measured value of the refractive power of the subject's eye E.

The fine focus adjustment is performed on the basis of interference sensitivity of OCT measurement. For example, the fine focus adjustment can be performed by: monitoring interference intensity (interference sensitivity) of interference signal acquired by performing OCT measurement of the subject's eye E; searching the position of the photography focusing lens 43 so as to maximize the interference intensity; and moving the photography focusing lens 43 to the searched position.

To perform the optical path length difference adjustment, the optical system is controlled so that a predetermined position on the subject's eye E is a reference position of a measurement range in the depth direction. The control is performed on at least one of the optical path length changing units 41 and 114. Thereby, the difference of the optical path length between the measurement optical path and the reference optical path is adjusted. By setting the reference position in the optical path length difference adjustment, OCT measurement can be performed with high accuracy over a desired measurement range in the depth direction simply by changing the wavelength sweep speed.

To perform the polarization adjustment, the polarization state of the reference light LR is adjusted for optimizing the interference efficiency between the measurement light LS and the reference light LR.

Storage Unit

The storage unit 212 stores various types of data. Examples of the data stored in the storage unit 212 include image data of an OCT image, image data of a fundus image, image data of an anterior segment image, and subject's eye information. The subject's eye information includes information on the subject such as patient ID and name, and information on the subject's eye such as identification information of the left eye/right eye.

Further, the storage unit 212 stores timing information 212A in advance. The timing information 212A includes timing information that defines an execution timing of A-scan. The information that defines the execution timing may be information that defines interval(s) of the execution timing(s) of A-scan(s) or information that defines the execution timing(s) of each of a plurality of A-scans. In the embodiments, the timing information 212A is timing information that defines the execution timings of A-scan so that the measurement light, which is deflected at substantially equal deflection angle intervals in the B-scan direction, is projected onto the measurement sites of the subject's eye E. The main controller 211 can perform A-scan on the subject's eye E based on the timing information 212A.

In some embodiments, the timing information 212A includes timing information of A-scan with reference to a reference timing of the deflection operation of the optical scanner 42. The reference timing is a timing at which the optical scanner 42 is in a state of deflecting the measurement light LS at a predetermined deflection angle. In this case, the main controller 211 can perform A-scan on the subject's eye E at the timing specified using the timing information 212A.

The timing information 212A is provided corresponding to the scan mode. That is, the storage unit 212 stores, in advance, the timing information 212A associated with the scan mode. In this case, the timing information 212A includes information that defines the execution timing(s) of A-scan performed in the scan mode.

In addition, the storage unit 212 stores various kinds of computer programs and data for operating the ophthalmologic apparatus 1.

The ophthalmologic apparatus 1 is provided with the user interface 240 for accepting an operation from the user or presenting information to the user. The controller 210 can control the user interface 240 to manage interface processing with the user.

Image Forming Unit

The image forming unit 220 forms an OCT image (image data) of the subject's eye E based on the sampling data obtained by sampling the detection signal from the detector 125 using the DAQ 130. As with the conventional swept source OCT, the image formation process includes noise removal (noise reduction), filtering, dispersion compensation, fast Fourier transform (FFT), and the like. In the case of employing an OCT apparatus of another type, the image forming unit 220 performs known processing according to the type employed.

The image forming unit 220 that functions as above includes, for example, a microprocessor, RAM, ROM, a hard disk drive, a circuit board, and the like. In a storage device such as the hard disk drive, a computer program for causing the processor to execute the functions described above is stored in advance. Note that "image data" and an "image" based on the image data may not be distinguished from each other in the present specification.

Data Processor

The data processor 230 processes data acquired through photography of the subject's eye E or data acquired through OCT measurement.

The data processor 230 performs various kinds of image processing and various kinds of analysis processing on the image formed by the image forming unit 220. For example, the data processor 230 performs various types of image correction such as brightness correction. The data processor 230 performs various kinds of image processing and various kinds of analysis on images captured by the fundus camera unit 2 (e.g., fundus images, anterior segment images, etc.).

For example, the data processor 230 performs known image processing such as interpolation for interpolating pixels in tomographic images to form three-dimensional image data of the fundus Ef Note that image data of a three-dimensional image means image data in which the position of a pixel is defined by a three-dimensional coordinate system. Examples of the image data of the three-dimensional image include image data defined by voxels three-dimensionally arranged. Such image data is referred to as volume data or voxel data. When displaying an image based on volume data, the data processor 230 performs rendering (volume rendering, maximum intensity projection (MIP), etc.) on the volume data, thereby forming image data of a pseudo three-dimensional image viewed from a particular line of sight. This pseudo three-dimensional image is displayed on the user interface 240 (display unit 240A).

The three-dimensional image data may be stack data of a plurality of tomographic images. The stack data is image data formed by three-dimensionally arranging tomographic images along a plurality of scan lines based on positional relationship of the scan lines. That is, the stack data is image data formed by representing tomographic images, which are originally defined in their respective two-dimensional coordinate systems, by a single three-dimensional coordinate system. That is, the stack data is image data formed by embedding tomographic images into a single three-dimensional space.

The data processor 230 can form a B-mode image (longitudinal cross-sectional image, axial cross-sectional image) in an arbitrary cross section, a C-mode image (transverse section image, horizontal cross-sectional image) in an arbitrary cross section, a projection image, a shadowgram, etc., by performing various renderings on the acquired three-dimensional data set (volume data, stack data, etc.). An image in an arbitrary cross section such as the B-mode image or the C-mode image is formed by selecting pixels (voxels) on a designated cross section from the three-dimensional data set. The projection image is formed by projecting the three-dimensional data set in a predetermined direction (z direction, depth direction, axial direction). The shadowgram is formed by projecting a part of the three-dimensional data set (for example, partial data corresponding to a specific layer) in a predetermined direction. An image having a viewpoint on the front side of the subject's eye, such as the C-mode image, the projection image, and the shadowgram, is called a front image (en-face image).

The data processor 230 can build (form) the B-mode image or the front image (blood vessel emphasized image, angiogram) in which retinal blood vessels and choroidal blood vessels are emphasized (highlighted), based on data (for example, B-scan image data) acquired in time series by OCT. For example, the OCT data in time series can be acquired by repeatedly scanning substantially the same site of the subject's eye E.

In some embodiments, the data processor 230 compares the B-scan images in time series acquired by B-scan for substantially the same site, converts the pixel value of a change portion of the signal intensity into a pixel value corresponding to the change portion, and builds the emphasized image in which the change portion is emphasized. Further, the data processor 230 forms an OCTA image by extracting information of a predetermined thickness at a desired site from a plurality of built emphasized images and building as an en-face image.

An image (for example, a three-dimensional image, a B-mode image, a C-mode image, a projection image, a shadowgram, and an OCTA image) generated by the data processor 230 is also included in the OCT image.

Further, the data processor 230 determines the focus state of the measurement light LS in focus adjustment by analyzing the detection result of the interference light obtained by the OCT measurement. For example, the main controller 211 performs repetitive OCT measurements while controlling the focusing driver 43A according to a predetermined algorithm. The data processor 230 analyzes detection results of interference light LC repeatedly acquired by the OCT measurements to calculate predetermined evaluation values relating to image quality of OCT images. The data processor 230 determines whether the calculated evaluation value is equal to or less than a threshold. In some embodiments, the fine focus adjustment is continued until the calculated evaluation value becomes equal to or less than the threshold. That is, when the evaluation value is equal to or less than the threshold, it is determined that the focus state of the measurement light LS is appropriate. And the fine focus adjustment is continued until it is determined that the focus state of the measurement light LS is appropriate.

In some embodiments, the main controller 211 monitors the intensity of the interference signal (interference intensity, interference sensitivity) acquired sequentially while acquiring the interference signal by performing the repetitive OCT measurements described above. In addition, while performing this monitoring process, the OCT focusing lens 43 is moved to find the position of the OCT focusing lens 43 in which the interference intensity is maximized. With the fine focus adjustment thus performed, the OCT focusing lens 43 can be guided to the position where the interference intensity is optimized.

Further, the data processor 230 determines the polarization state of at least one of the measurement light LS and the reference light LR by analyzing the detection result of the interference light obtained by the OCT measurement. For example, the main controller 211 performs repetitive OCT measurements while controlling at least one of the polarization controllers 103 and 118 according to a predetermined algorithm. In some embodiments, the main controller 211 controls the attenuator 120 to change an attenuation of the reference light LR. The data processor 230 analyzes detection results of interference light LC repeatedly acquired by the OCT measurements to calculate predetermined evaluation values relating to image quality of OCT images. The data processor 230 determines whether the calculated evaluation value is equal to or less than a threshold. The threshold is set in advance. Polarization adjustment is continued until the evaluation value calculated becomes equal to or less than the threshold. That is, when the evaluation value is equal to or less than the threshold, it is determined that the polarization state of the measurement light LS is appropriate. And the polarization adjustment is continued until it is determined that the polarization state of the measurement light LS is appropriate.

In some embodiments, the main controller 211 can monitor the interference intensity also in the polarization adjustment.

Further, the data processor 230 performs predetermined analysis processing on the detection result of the interference light acquired by the OCT measurement or the OCT image formed based on the detection result. Examples of the predetermined analysis processing include specifying (identification) of a predetermined site (tissue, lesion) of the subject's eye E; calculation of a distance between designated sites (distance between layers, interlayer distance), area, angle, ratio, or density; calculation by a designated formula; specifying of the shape of a predetermined site; calculation of these statistics; calculation of distribution of the measured value or the statistics; image processing based on these analysis processing results, and the like. Examples of the predetermined tissue include a blood vessel, an optic papilla, a central fovea, a macula, and the like. Examples of the predetermined lesion include a leukoma, a hemorrhage, and the like.

The data processor 230 that functions as above includes, for example, a processor described above, a RAM, a ROM, a hard disk drive, a circuit board, and the like. In a storage device such as the hard disk drive, a computer program for causing the processor to execute the functions described above is stored in advance.

User Interface

The user interface 240 includes the display unit 240A and the operation unit 240B. The display unit 240A includes the aforementioned display device of the arithmetic control unit 200 and the display device 3. The operation unit 240B includes the aforementioned operation device of the arithmetic control unit 200. The operation unit 240B may include various types of buttons and keys provided on the case of the ophthalmologic apparatus 1 or the outside. For example, when the fundus camera unit 2 has a case similar to that of the conventional fundus camera, the operation unit 240B may include a joy stick, an operation panel, and the like provided to the case. Besides, the display unit 240A may include various types of display devices such as a touch panel and the like arranged on the case of the fundus camera unit 2.

Note that the display unit 240A and the operation unit 240B need not necessarily be formed as separate devices. For example, a device like a touch panel, which has a display function integrated with an operation function, can be used. In such cases, the operation unit 240B includes the touch panel and a computer program. The content of operation performed on the operation unit 240B is fed to the controller 210 in the morphology of an electrical signal. Moreover, operations and inputs of information may be performed by using a graphical user interface (GUI) displayed on the display unit 240A and the operation unit 240B.

Figure 4:
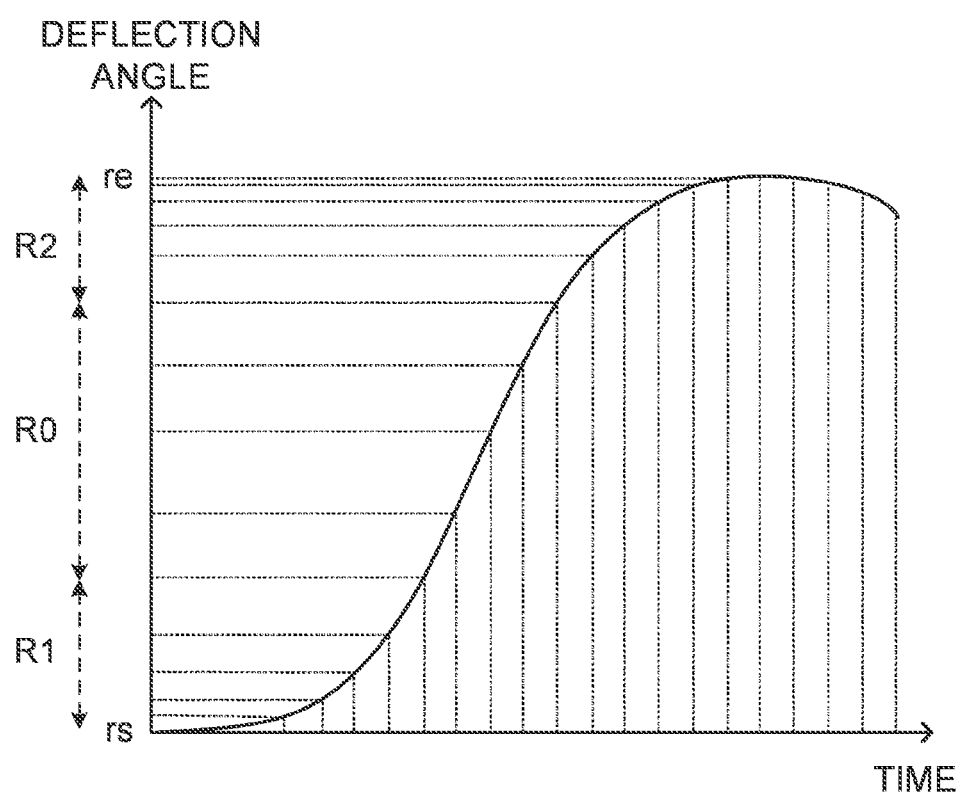
FIG. 4 is a schematic diagram illustrating an example of the operating characteristics of the optical scanner according to the embodiments.
Figure 5:
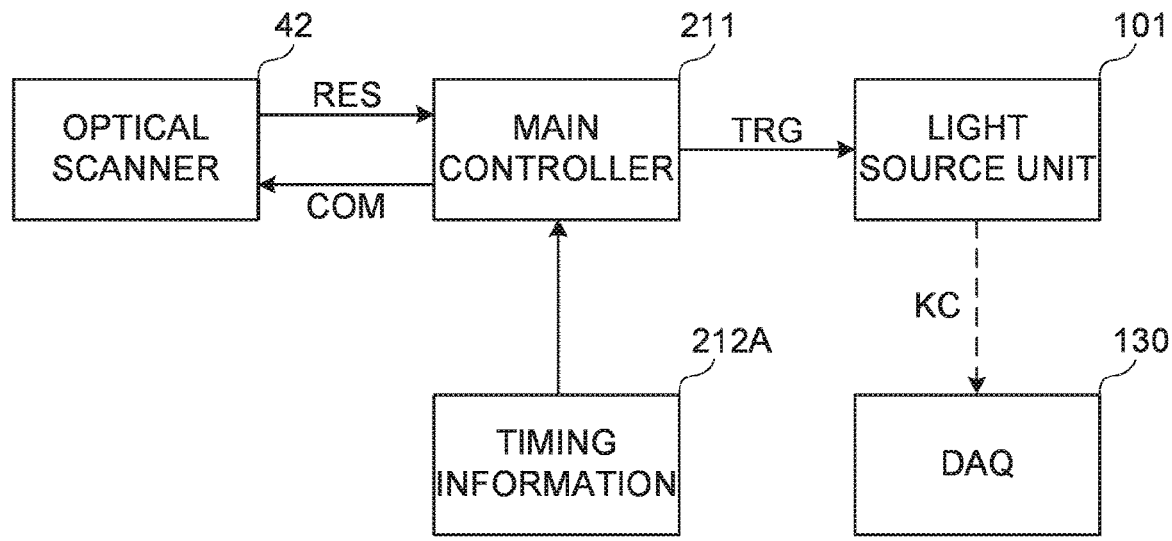
FIG. 5 is a schematic diagram for explaining processing performed by the ophthalmologic apparatus according to the embodiments.
Figure 6:
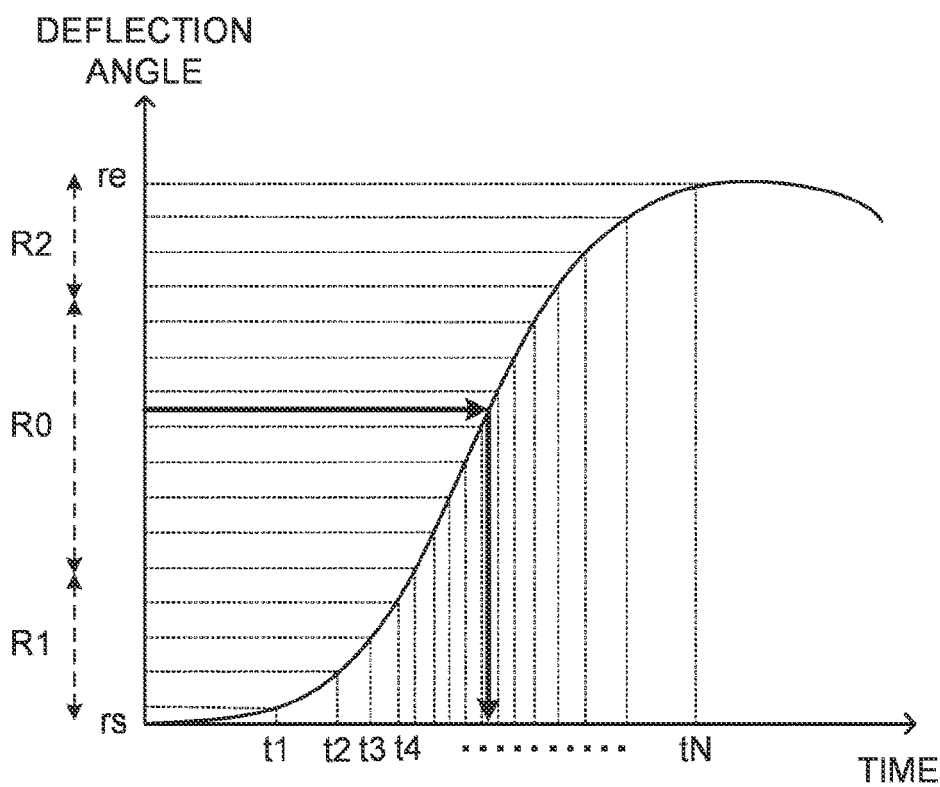
FIG. 6 is a schematic diagram for explaining processing performed by the ophthalmologic apparatus according to the embodiments.
Figure 7:
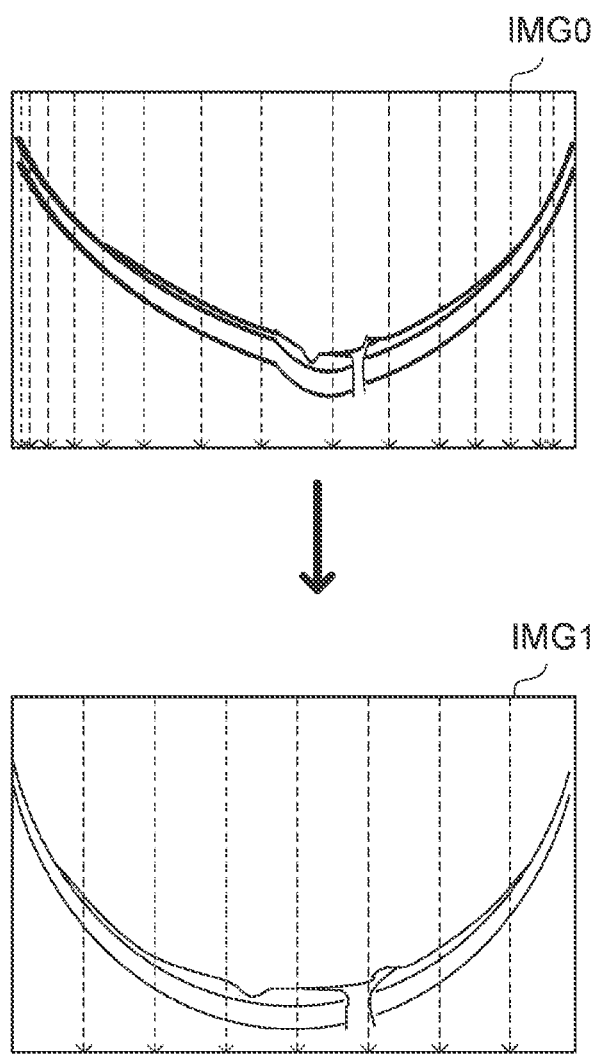
FIG. 7 is a schematic diagram for explaining processing performed by the ophthalmologic apparatus according to the embodiments.

FIGS. 4 to 7 show diagrams describing the operation of the ophthalmologic apparatus 1 according to the first embodiment. FIG. 4 schematically represents deflection angle versus time characteristics of the optical scanner 42. In FIG. 4, the horizontal axis represents the time corresponding to the execution timing of the A-scan (data set acquisition timing), and the vertical axis represents the deflection angle. FIG. 5 is a schematic diagram for explaining a configuration of the ophthalmologic apparatus 1 according to the first embodiment. In FIG. 5, like reference numerals designate like parts as in FIG. 2 or FIG. 3. The same description may not be repeated. FIG. 6 shows a diagram describing the operation of the controller 210 according to the first embodiment. In FIG. 6, like reference numerals designate like parts as in FIG. 4. The same description may not be repeated. FIG. 7 schematically shows a tomographic image fundus Ef of the subject's eye E. It should be noted that the number of A-scans in the tomographic images IMG0 and IMG1 is illustrative in FIG. 7, and is not limited to that number.

The optical scanner 42 includes a mirror that reflects the measurement light LS. The optical scanner 42 deflects the measurement light LS in a predetermined deflection angle range by swinging (rocking) the mirror back and forth in a swing direction corresponding to a predetermined deflection direction. As shown in FIG. 4, the deflection angle range is a range between a deflection start angle rs (first deflection angle) and a deflection end angle re (second deflection angle). Such the optical scanner 42 includes a galvano scanner, a resonant mirror, or the like. That is, the deflection angle range of the optical scanner 42 includes a linear operation range R0 and non-linear operation ranges R1 and R2. In the linear operation range R0, the deflection angle changes approximately linearly with changes in the data set acquisition timing (time changes). In each of the non-linear operation ranges R1 and R2, the deflection angle does not change approximately linearly with changes in the data set acquisition timing. The non-linear operation range R1 includes the deflection start angle rs. The non-linear operation range R2 includes the deflection end angle re.

In the case that the operating characteristics as shown in FIG. 4 are provided, when the A-scan is executed at regular intervals in time, the deflection angle intervals become non-uniform. Thereby, a tomographic image IMG0 of the fundus Ef as shown in FIG. 7 is obtained from the acquired data set group in the A-scan direction. In the tomographic image IMG0 shown in FIG. 7, due to the non-linear operation of the optical scanner 42 described above, the deflection angle intervals become narrower in the non-linear operation ranges R1, R2, and the deflection angle intervals becomes wider in the linear operation range R0. Therefore, in practice, it is impossible to form tomographic images using data set groups acquired in the non-linear operation ranges R1 and R2 where the degree of change in the deflection angle intervals is large. As a result, tomographic images need to be formed using the data set group acquired in the linear operation range R0. Increasing the deflection speed required for wide-angle, high-definition OCT measurement leads to extending the non-linear operating range. Thereby, this means that it is not possible to cope with a further increase in the deflection speed.

On the other hand, the main controller 211 controls the execution timings of the A-scan by outputting the control signal TRG to the light source unit 101 at the execution timings specified using the timing information 212A with reference to the reference timing of the deflection operation of the optical scanner 42. In some embodiments, the main controller 211 specifies the reference timing of the deflection operation of the optical scanner 42 by outputting the control signal COM to the optical scanner 42.

Thereby, when the main controller 211 outputs the control signal TRG to the light source unit 101, a wavelength sweeping operation is started in synchronization with the output timing of the control signal TRG. And the detection result of the interference light LC is acquired in the DAQ 130 in synchronization with the clock KC. That is, the main controller 211 can acquire data of the subject's eye E at scan positions scanned at substantially the same scan angle (intervals) by controlling the execution timing of the A-scan using the control signal TRG.

For example, as shown in FIG. 6, the timing information 212A is stored in the storage unit 212 in advance. The timing information 212A defines the execution timings t1, t2, t3, . . . , tN (N is an integer equal to or greater than 2) of A-scans so that the intervals of the deflection angle are substantially equal in the entire deflection angle range including the linear operation range R0, the non-linear operation ranges R1 and R2.

In some embodiments, the timing information 212A is specified in advance from the operating characteristics of the optical scanner 42, and is stored in the storage unit 212. For example, the timing information 212A is stored before the shipping process, the inspection process, or the OCT measurement. For example, the main controller 211 controls the deflection operation of the optical scanner 42 by outputting a control signal including information representing a control waveform that defines the deflection operation of the mirror for deflecting the measurement light LS to the optical scanner 42. Further, the main controller 211 outputs a control signal COM to the optical scanner 42 to receive a response signal RES including an operation state such as a deflection angle of the optical scanner 42, and monitors a state of the deflection operation of the optical scanner 42 based on the received response signal RES to specify the timing information 212A. The main controller 211 stores the specified timing information 212A in the storage unit 212.

As described above, according to the first embodiment, A-scan data based on the measurement light LS deflected by the optical scanner 42 at substantially equal intervals in the entire deflection angle range can be acquired. Thereby, the tomographic image IMG1 of the fundus Ef as shown in FIG. 7 can be obtained. The tomographic image IMG1 shown in FIG. 7 is formed from the data set group acquired using the measurement light LS deflected at substantially equal intervals in the deflection angle range, regardless of non-linear operation of the optical scanner 42 described above. Therefore, a tomographic image can be formed using a data set group acquired not only in the linear operation range R0 but also in the non-linear operation ranges R1 and R2 (at least a part thereof). That is, even if the deflection speed is increased, a part of the non-linear operation range can be utilized. Thereby, it becomes possible to cope with a further increase in the deflection speed.

The optical system, which is includes in the OCT unit 100, in the path from the interference optical system to the objective lens 22 is an example of the "acquisition unit" according to the embodiments.

Operation Example

The operation of the ophthalmologic apparatus 1 according to the first embodiment will be described.

Figure 8:
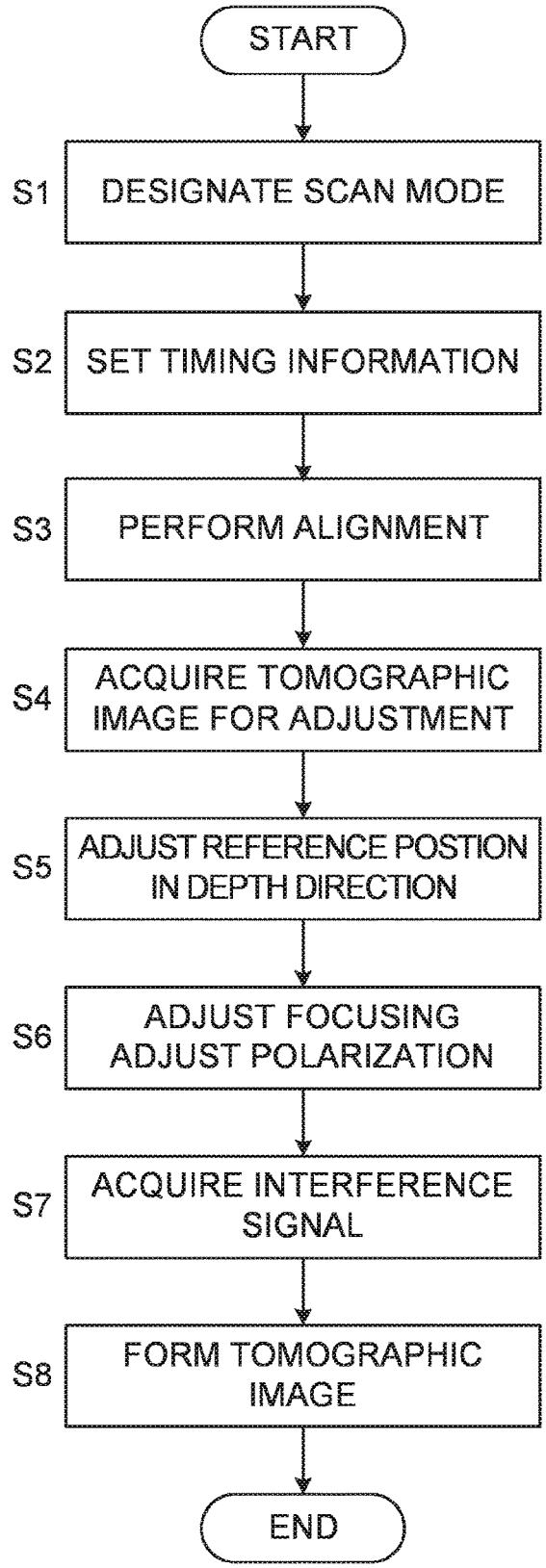
FIG. 8 is a flowchart illustrating an example of the operation of the ophthalmologic apparatus of the embodiments.

FIG. 8 shows an example of the operation of the ophthalmologic apparatus 1 according to the embodiments. FIG. 8 shows a flowchart of an example of the operation of the ophthalmologic apparatus 1 according to the first embodiment. The storage unit 212 stores computer programs for realizing the processing shown in FIG. 8. The main controller 211 operates according to the computer programs, and thereby the main controller 211 performs the processing shown in FIG. 8.

S1: Designate Scan Mode

The main controller unit 211 accepts designation of a scan mode from the user.

The user can designate the scan mode or the operation mode by operating the operation unit 240B. When the scan mode is designated by operating the operation unit 240B by the user, the main controller 211 analyzes an operation information from the operation unit 240B to specify the designated scan mode. When the operation mode is designated by operating the operation unit 240B by the user, the main controller 211 analyzes an operation information from the operation unit 240B to specify a scan mode designated in advance in the designated operation mode.

S2: Set Timing Information

The main controller 211 specifies the timing information 212A stored in the storage unit 212 corresponding to the scan mode designated in step S1, and sets it as timing information to be referred to during the scan.

For example, the main controller 211 outputs the control signal including information representing the control waveform that defines the deflection operation of the mirror for deflecting the measurement light LS to the optical scanner 42 at an arbitrary timing between step S2 and step S7 described later. In each step from step S4 to step S7, the main controller 211 may output a control signal including information representing predetermined control waveforms different from each other, or may output a control signal including information representing the same predetermined control waveform.

S3: Perform Alignment

Next, the main controller 211 performs alignment.

That is, the main controller 211 controls the alignment optical system 50 to project the alignment indicator onto the subject's eye E. At this time, a fixation target generated by the LCD 39 is also projected onto the subject's eye E. The main controller 211 controls the movement mechanism 150 based on the movement amount of the optical system to relatively move the optical system with respect to the subject's eye E by the movement amount. The movement amount is specified based on the receiving light image obtained using the image sensor 35, for example. The main controller 211 repeatedly executes this processing.

In some embodiments, the rough alignment adjustment and the fine alignment adjustment are performed after the alignment in step S3 is completed.

S4: Acquire Tomographic Image for Adjustment

The main controller 211 causes the LCD 39 to display the fixation target for OCT measurement at a predetermined position on the LCD 39. The main controller 211 can display the fixation target at a display position on the LCD 39 corresponding to a position of an optical axis of the optical axis on the fundus Ef.

Subsequently, the main controller 211 controls the OCT unit 100 to perform OCT provisional measurement, and to acquire a tomographic image for adjustment for adjusting the reference position of the measurement range in the depth direction. Specifically, the main controller 211 controls the optical scanner 42 to deflect the measurement light LS generated based on the light L0 emitted from the light source unit 101 at a predetermined timing and to scan a predetermined site (for example, fundus) of the subject's eye E with the deflected measurement light LS. The detection result of the interference light obtained by scanning with the measurement light LS is sent to the image forming unit 220 after being sampled in synchronization with the clock KC. The image forming unit 220 forms the tomographic image (OCT image) of the subject's eye E from the obtained interference signal.

S5: Adjust Reference Position in Depth Direction

Subsequently, the main controller 211 adjusts the reference position of the measurement range in the depth direction (z direction).

For example, the main controller 211 causes the data processor 230 to specify a predetermined site (for example, sclera) in the tomographic image obtained in step S4, and sets a position separated by a predetermined distance in the depth direction from the specified position of the predetermined site as the reference position of the measurement range. Alternatively, a predetermined position determined in advance so that the optical path lengths of the measurement light LS and the reference light LR substantially coincide may be set as the reference position of the measurement range.

S6: Adjust Focusing, Adjust Polarization

Next, the main controller 211 perform control of adjusting focusing and of adjusting polarization.

For example, the main controller 211 controls the OCT unit 100 including the light source unit 101 to perform OCT measurement at a predetermined timing after controlling the focusing driver 43A to move the OCT focusing lens 43 by a predetermined distance. The main controller 211 causes the data processor 230 to determine the focus state of the measurement light LS based on the detection result of the interference light acquired by the OCT measurement, as described above. When it is determined that the focus state is not appropriate based on the determination result of the data processor 230, the main controller 211 controls the focusing driver 43A again and repeats this until it is determined that the focus state of the measurement light LS is appropriate.

Further, for example, the main controller 211 controls the OCT unit 100 including the light source unit 101 to perform OCT measurement at a predetermined timing after controlling at least one of the polarization controllers 103 and 118 to change the polarization state of at least one of the light L0 and the measurement light LS by a predetermined amount. And then, the main controller 211 causes the image forming unit 220 to form the OCT image on the basis of the detection result of the acquired interference light. The main controller 211 causes the data processor 230 to determine the image quality of the OCT image acquired by the OCT measurement, as described above. When it is determined that the polarization state is not appropriate based on the determination result of the data processor 230, the main controller 211 controls the polarization controllers 103 and 118 again and repeats this until it is determined that the polarization state of the measurement light LS is appropriate.

S7: Acquire Interference Signal

Subsequently, the main controller 211 performs OCT measurement (at least A-scan) on the fundus Ef by outputting the control signal TRG to the light source unit 101 at the execution timings specified based on the timing information set in step S2 with reference to the reference timing of the deflection operation of the optical scanner 42. The detection result of the interference light acquired by the OCT measurement is sampled by the DAQ 130 and is stored as the interference signal in the storage unit 212 or the like.

S8: Form Tomographic Image

Next, the main controller 211 causes the image forming unit 220 to form the data set group of the A-scan image data of the fundus Ef based on the interference signal acquired in step S7. The main controller 211 can cause the display unit 240A to display the B-scan image (tomographic image of FIG. 7) based on the data set group of the generated A-scan image.

This terminates the operation of the ophthalmologic apparatus 1 (END).

Second Embodiment

In the first embodiment, the case in which the ophthalmologic apparatus 1 performs OCT measurement on the subject's eye E by performing feed-forward control has been described. However, the configuration of the ophthalmologic apparatus according to the embodiments is not limited thereto. The ophthalmologic apparatus 1 according to a second embodiment performs OCT measurement by performing feed-back control on the subject's eye E.

Hereinafter, the ophthalmologic apparatus 1 according to the second embodiment will be described mainly about the differences from the first embodiment.

The ophthalmologic apparatus 1 according to the second embodiment is almost the same configuration as that of the first embodiment. The difference between the ophthalmologic apparatus 1 according to the second embodiment and the ophthalmologic apparatus 1 according to the first embodiment is that OCT measurement is performed depending on the deflection operation state of the optical scanner 42 without referring to the timing information 212A.

Figure 9:
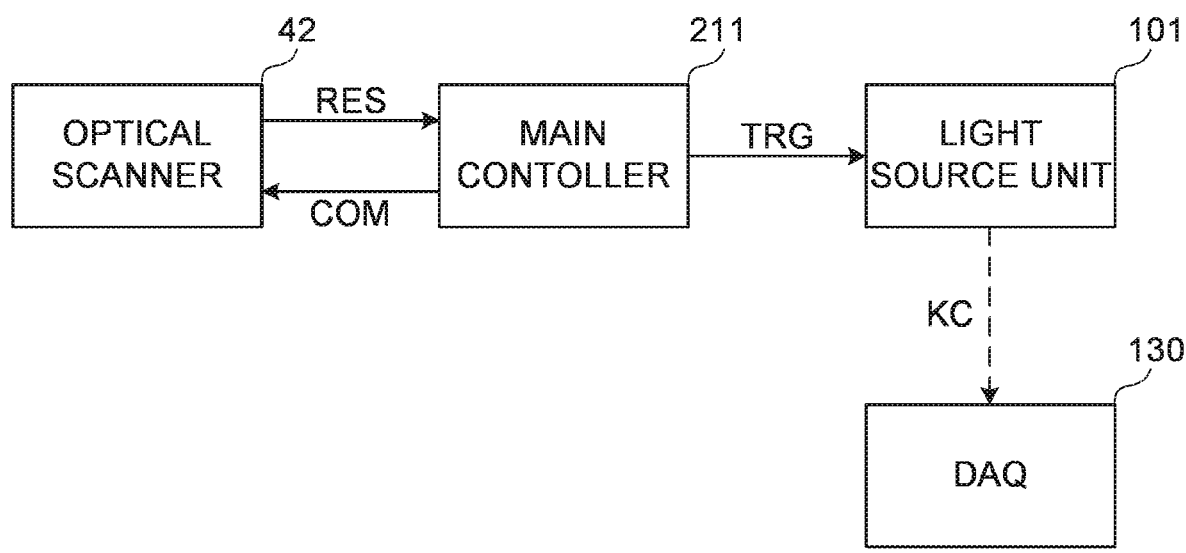
FIG. 9 is a schematic diagram for explaining processing performed by the ophthalmologic apparatus according to the embodiments.

FIG. 9 shows a diagram describing the operation of the controller 210 according to the second embodiment. In FIG. 9, like reference numerals designate like parts as in FIG. 6. The same description may not be repeated.

In the second embodiment, the ophthalmologic apparatus 1 performs OCT measurement (at least A-scan) depending on the deflection angle of the of the optical scanner 42. Specifically, the main controller 211 acquires operation information representing a deflection angle from the optical scanner 42, determines whether or not the deflection angle is a predetermined deflection angle based on the acquired operation information, and controls the OCT unit 100 to perform A-scan when it is determined that the deflection angle is the predetermined deflection angle. The predetermined deflection angle is determined in advance.

That is, the main controller 211 receives the response signal RES including the operation information by outputting the control signal COM to the optical scanner 42, and specifies the deflection angle of the mirror from the operation information included in the received response signal RES. The main controller 211 determines whether or not the deflection angle of the mirror is a predetermined deflection angle based on the acquired operation information, and controls the OCT unit to perform A-scan by outputting the control signal TRG to the light source unit 101 when it is determined that the deflection angle is the predetermined deflection angle.

When the main controller 211 outputs the control signal TRG to the light source unit 101, a wavelength sweeping operation is started in synchronization with the output timing of the control signal TRG. And the detection result of the interference light LC is acquired in the DAQ 130 in synchronization with the clock KC.

Operation Example

The operation of the ophthalmologic apparatus 1 according to the second embodiment will be described.

Figure 10:
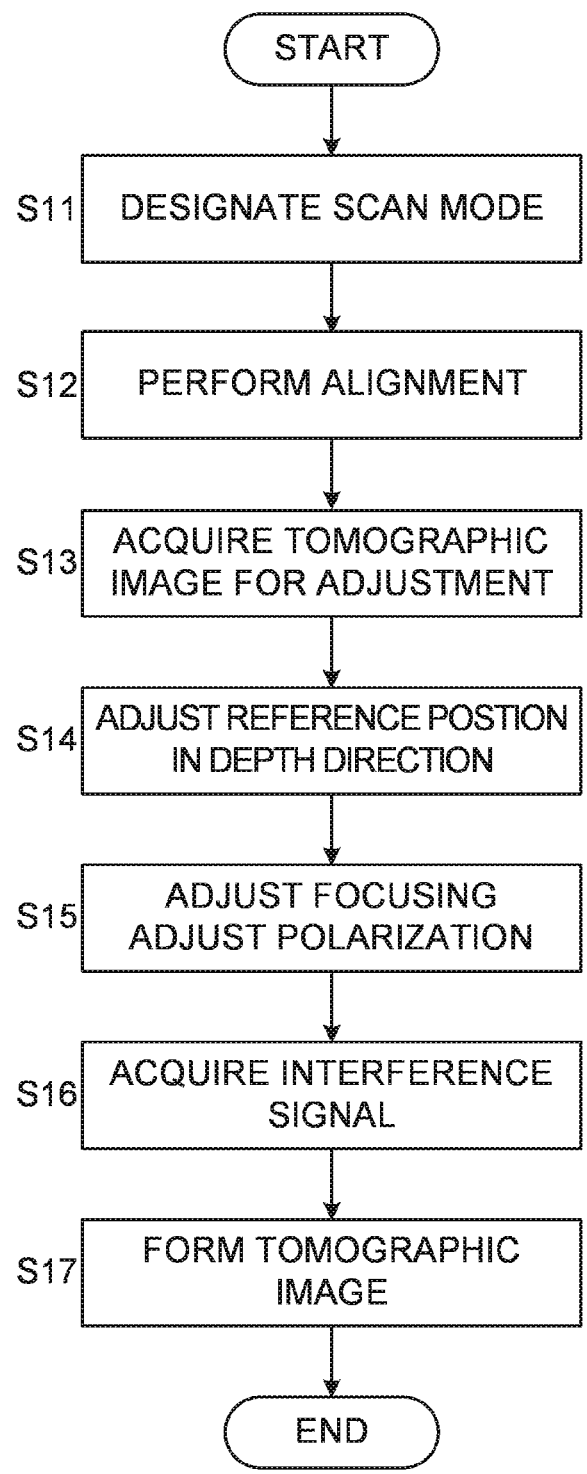
FIG. 10 is a flowchart illustrating an example of the operation of the ophthalmologic apparatus of the embodiments.

FIG. 10 shows an example of the operation of the ophthalmologic apparatus 1 according to the embodiments. FIG. 10 shows a flowchart of a first example of the operation of the ophthalmologic apparatus 1 according to the second embodiment. The storage unit 212 stores computer programs for realizing the processing shown in FIG. 10. The main controller 211 operates according to the computer programs, and thereby the main controller 211 performs the processing shown in FIG. 10.

S11: Designate Scan Mode

The main controller unit 211 accepts designation of a scan mode from the user, in the same manner as step S1.

S12: Perform Alignment

Next, the main controller 211 performs alignment, in the same manner as step S3.

S13: Acquire Tomographic Image for Adjustment

The main controller 211 causes the LCD 39 to display the fixation target for OCT measurement at a predetermined position on the LCD 39, in the same manner as step S4. Subsequently, the main controller 211 controls the OCT unit 100 to perform OCT provisional measurement, and to acquire a tomographic image for adjustment for adjusting the reference position of the measurement range in the depth direction.

S14: Adjust Reference Position in Depth Direction

Subsequently, the main controller 211 adjusts the reference position of the measurement range in the depth direction (z direction), in the same manner as step S5.

S15: Adjust Focusing, Adjust Polarization

Next, the main controller 211 performs control of adjusting focusing and of adjusting polarization, in the same manner as step S6.

S16: Acquire Interference Signal

Subsequently, the main controller 211 controls the OCT unit 100 to perform OCT measurement (at least A-scan) on the fundus Ef of the subject's eye E at the execution timings corresponding to the deflection angles by outputting the control signal TRG to the light source unit 101 depending on the deflection angles of the optical scanner 42.

Specifically, the main controller 211 acquires the deflection angle of the optical scanner 42 from the operation information included in the response signal RES periodically received from the optical scanner 42. Each time the deflection angle is acquired, the main controller 211 determines whether or not the deflection angle of the mirror is the predetermined deflection angle, and when it is determined that the deflection angle is the predetermined deflection angle, the main controller 211 performs A-scan by outputting the control signal TRG to the light source unit 101. Such control of performing A-scan using the control signal TRG is repeated within a predetermined scan range.

The detection result of the interference light acquired by the OCT measurement is sampled by the DAQ 130 and is stored as the interference signal in the storage unit 212 or the like.

S17: Form Tomographic Image

Next, the main controller 211 causes the image forming unit 220 to form the data set group of the A-scan image of the fundus Ef based on the interference signal acquired in step S16, in the same manner as step S8.

This terminates the operation of the ophthalmologic apparatus 1 (END).

Third Embodiment

In the first embodiment or the second embodiment, the case in which the A-scan is performed so that the fundus Ef is mainly scanned at substantially equal deflection angle intervals. However, the configuration of the ophthalmologic apparatus according to the embodiments is not limited thereto.

The ophthalmologic apparatus 1 according to a third embodiment performs A-scan so that mainly the anterior segment Ea is mainly scanned at substantially equal scan intervals (so that the intervals between the projection positions of the measurement light LS on the anterior segment Ea are substantially equal).

For example, the ophthalmologic apparatus 1 according to the third embodiment is almost the same configuration as that of the first embodiment or the second embodiment. In this case, in the third embodiment, a front lens is disposed between the objective lens 22 and the subject's eye E in the ophthalmologic apparatus 1 according to the first embodiment or the second embodiment. Thereby, the anterior segment Ea of the subject's eye E is irradiated with the measurement light LS that is converted into a parallel light beam.

For example, in the third embodiment, the timing information 212A is set so that A-scans are performed at substantially equal scan intervals is stored in the storage unit 212. When the front lens is disposed between the objective lens 22 and the subject's eye E, the main controller 211 can perform A-scan at substantially equal scan intervals on the anterior segment Ea, by performing OCT measurement on the anterior segment Ea based on the timing information 212A.

For example, in the third embodiment, when the front lens is disposed between the objective lens 22 and the subject's eye E, the main controller 211 determines whether or not the deflection angle of the optical scanner 42 is a predetermined deflection angle. The predetermined deflection angle is determined in advance so that the scan intervals are substantially equal. When it is determined that the deflection angle is the predetermined deflection angle, the main controller 211 performs OCT measurement on the anterior segment Ea. Thereby, A-scans can be performed at substantially equal scan intervals on the anterior segment Ea.

In some embodiments, the operation mode of the ophthalmologic apparatus 1 includes a fundus measurement mode and an anterior segment measurement mode. For example, in the ophthalmologic apparatus 1 according to the first embodiment, the timing information 212A includes timing information for the fundus measurement mode and timing information for the anterior segment measurement mode. In the fundus measurement mode, A-scans are performed so as to scan at substantially equal scan angles (deflection angles) based on the timing information for the fundus measurement mode. In the anterior segment measurement mode, A-scans are performed so as to scan at substantially equal scan intervals based on the timing information for the anterior segment measurement mode.

For example, in the ophthalmologic apparatus 1 according to the second embodiment, it is configured to be capable of determining whether or not the deflection angle of the optical scanner 42 is a predetermined deflection angle for the fundus measurement mode. The predetermined deflection angle for the fundus measurement mode is one of deflection angles set so as to scan at substantially equal scan angles (deflection angles). Thereby, when it is determined that the deflection angle of the optical scanner 42 is the predetermined deflection angle for the fundus measurement angle, A-scans are performed so as to scan at substantially equal scan angles (deflection angles). Further, in the ophthalmologic apparatus 1 according to the second embodiment, it is configured to be capable of determining whether or not the deflection angle of the optical scanner 42 is a predetermined deflection angle for the anterior segment measurement mode. The predetermined deflection angle for the anterior segment measurement mode is one of deflection angles set so as to scan at substantially equal scan intervals. Thereby, when it is determined that the deflection angle of the optical scanner 42 is the predetermined deflection angle for the anterior segment measurement angle, A-scans are performed so as to scan at substantially equal scan intervals.

In the embodiments described above, the case where the optical scanner 42 includes a galvano scanner has been described. However, the configuration according to the embodiments is not limited thereto. For example, the optical scanner 42 may include a resonant mirror.

Effects

The ophthalmologic apparatus and the method of controlling the ophthalmologic apparatus according to the embodiments are explained.

An ophthalmologic apparatus (1) according to some embodiments includes an acquisition unit (optical system included in the OCT unit 100 in the path from the interference optical system to the objective lens 22), and a controller (210, main controller 211). The acquisition unit includes an optical scanner (42) capable of deflecting light in a predetermined deflection angle range. The acquisition unit is configured to acquire data (OCT data) of a subject's eye (E) by performing A-scan on the subject's eye using optical coherence tomography by measurement light (LS) deflected by the optical scanner. The controller is configured to cause the acquisition unit to perform A-scan based on a deflection operation state of the optical scanner.

According to such a configuration, A-scan can be performed when the deflection operation state of the optical scanner is in a desired state. Thereby, regardless of the operating characteristics of the optical scanner, data at a desired scan position in the measurement site can be acquired.

The ophthalmologic apparatus according to some embodiments includes a storage unit (212) configured to store timing information (212A) of the A-scan in advance, wherein the controller is configured to cause the acquisition unit to perform A-scan based on the timing information.

According to such a configuration, regardless of the operating characteristics of the optical scanner, A-scan can be performed at a desired timing with simple feed-forward control.

In the ophthalmologic apparatus according to some embodiments, the timing information includes timing information of A-scan with reference to a reference timing of deflection operation of the optical scanner. The controller is configured to cause the acquisition unit to perform A-scan at a timing specified by the timing information.

According to such a configuration, A-scan can be performed at a desired timing with reference to the reference timing of the deflection operation of the optical scanner with simple feed-forward control.

In the ophthalmologic apparatus according to some embodiments, the controller is configured to cause the acquisition unit to perform A-scan depending on a deflection angle of the optical scanner.

According to such a configuration, regardless of the operating characteristics of the optical scanner, A-scan can be performed depending on the deflection angle of the optical scanner. Thereby, A-scan can be performed with simple feed-back control.

In the ophthalmologic apparatus according to some embodiments, the controller is configured: to acquire operation information representing a deflection angle of the optical scanner; to determine whether or not the deflection angle is a predetermined deflection angle based on the acquired operation information; and to cause the acquisition unit to perform A-scan when it is determined that the deflection angle is the predetermined deflection angle.

According to such a configuration, A-scan can be performed when the deflection angle of the optical scanner is a desired deflection angle. Thereby, regardless of the operating characteristics of the optical scanner, data at a desired scan position can be acquired.

In the ophthalmologic apparatus according to some embodiments, the controller is configured to cause the acquisition unit to perform A-scan so that intervals between the deflection angles are substantially equal.

According to such a configuration, data at scan positions scanned at substantially equal deflection angle intervals can be acquired. Thereby, data at substantially uniform positions in curved shape such as the fundus can be acquired.

In the ophthalmologic apparatus according to some embodiments, the controller is configured to cause the acquisition unit to perform A-scan so that intervals between projection positions of the measurement light on the subject's eye are substantially equal.

According to such a configuration, data at scan positions scanned at substantially equal scan intervals can be acquired. Thereby, data at substantially uniform positions can be acquired at sites scanned with a parallel light beam such as the anterior segment.

A method of controlling an ophthalmologic apparatus (1) according to some embodiments is the method of controlling the ophthalmologic apparatus including an optical scanner (42) capable of deflecting light in a predetermined deflection angle range. The method of the ophthalmologic apparatus includes: an acquisition step of acquiring data (OCT data) of a subject's eye (E) by performing A-scan on the subject's eye using optical coherence tomography by measurement light (LS) deflected by the optical scanner; and a control step of performing A-scan based on a deflection operation state of the optical scanner.

According to such a method, A-scan can be performed when the deflection operation state of the optical scanner is in a desired state. Thereby, regardless of the operating characteristics of the optical scanner, data at a desired scan position in the measurement site can be acquired.

In the method of controlling the ophthalmologic apparatus according to some embodiments, the control step performs A-scan based on timing information of the A-scan stored in advance.

According to such a method, regardless of the operating characteristics of the optical scanner, A-scan can be performed at a desired timing with simple feed-forward control.

In the method of controlling the ophthalmologic apparatus according to some embodiments, the timing information includes timing information of A-scan with reference to a reference timing of deflection operation of the optical scanner, and the control step performs A-scan at a timing specified by the timing information.

According to such a method, A-scan can be performed at a desired timing with reference to the reference timing of the deflection operation of the optical scanner with simple feed-forward control.

In the method of controlling the ophthalmologic apparatus according to some embodiments, the control step performs A-scan depending on a deflection angle of the optical scanner.

According to such a method, regardless of the operating characteristics of the optical scanner, A-scan can be performed depending on the deflection angle of the optical scanner. Thereby, A-scan can be performed with simple feed-back control.

In the method of controlling the ophthalmologic apparatus according to some embodiments, the control step includes: an operation information acquisition step that acquires operation information representing a deflection angle of the optical scanner; a determination step that determines whether or not the deflection angle is a predetermined deflection angle based on the acquired operation information; and a performing step that performs A-scan when it is determined that the deflection angle is the predetermined deflection angle.

According to such a method, A-scan can be performed when the deflection angle of the optical scanner is a desired deflection angle. Thereby, regardless of the operating characteristics of the optical scanner, data at a desired scan position can be acquired.

In the method of controlling the ophthalmologic apparatus according to some embodiments, the control step performs A-scan so that intervals between the deflection angles are substantially equal.

According to such a method, data at scan positions scanned at substantially equal deflection angle intervals can be acquired. Thereby, data at substantially uniform positions in curved shape such as the fundus can be acquired.

In the method of controlling the ophthalmologic apparatus according to some embodiments, the control step performs A-scan so that intervals between projection positions of the measurement light on the subject's eye are substantially equal.

According to such a method, data at scan positions scanned at substantially equal scan intervals can be acquired. Thereby, data at substantially uniform positions can be acquired at sites scanned with a parallel light beam such as the anterior segment.

Others

In the above embodiments, the case where the swept source type OCT is used has been described. However, the spectral domain type OCT may be used. In this case, a low coherence light source (for example, an SLD light source etc.) is used instead of the wavelength sweeping light source, in the light source unit 101. And a spectrometer and an image sensor (for example, a CCD etc.) are used instead of the detector 125, in the interference optical system.

The above-described embodiments are merely examples for carrying out the present invention. Those who intend to implement the present invention can apply any modification, omission, addition, or the like within the scope of the gist of the present invention.

In some embodiments, a program for causing a computer to execute the method for controlling the ophthalmologic apparatus is provided. Such a program can be stored in any kind of recording medium that can be read by the computer. Examples of the recording medium include a semiconductor memory, an optical disk, a magneto-optical disk (CD-ROM, DVD-RAM, DVD-ROM, MO, etc.), a magnetic storage medium (hard disk, floppy (registered trade mark) disk, ZIP, etc.), and the like. The computer program may be transmitted and received through a network such as the Internet, LAN, etc.

The invention has been described in detail with particular reference to preferred embodiments thereof and examples, but it will be understood that variations and modifications can be effected within the spirit and scope of the invention covered by the claims which may include the phrase "at least one of A, B and C" as an alternative expression that means one or more of A, B and C may be used, contrary to the holding in Superguide v. DIRECTV, 69 USPQ2d 1865 (Fed. Cir. 2004).

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ophthalmologic apparatus, comprising
an acquisition unit including an optical scanner capable of deflecting light in a predetermined deflection angle range and configured to acquire data of a subject's eye by performing A-scan on the subject's eye using optical coherence tomography by measurement light deflected by the optical scanner; and
a controller configured to cause the acquisition unit to perform A-scan based on a deflection operation state of the optical scanner,
wherein the controller is configured to cause the acquisition unit to perform A-scan so that intervals between projection positions of the measurement light on the subject's eye are substantially equal.

2. The ophthalmologic apparatus of claim 1, further comprising
a storage unit configured to store timing information of the A-scan in advance, wherein
the controller is configured to cause the acquisition unit to perform A-scan based on the timing information.

3. The ophthalmologic apparatus of claim 2, wherein
the timing information includes timing information of A-scan with reference to a reference timing of deflection operation of the optical scanner, and
the controller is configured to cause the acquisition unit to perform A-scan at a timing specified by the timing information.

4. The ophthalmologic apparatus of claim 1, wherein
the controller is configured to cause the acquisition unit to perform A-scan depending on a deflection angle of the optical scanner.

5. The ophthalmologic apparatus of claim 4, wherein
the controller is configured:
to acquire operation information representing a deflection angle of the optical scanner;
to determine whether or not the deflection angle is a predetermined deflection angle based on the acquired operation information; and
to cause the acquisition unit to perform A-scan when it is determined that, the deflection angle is the predetermined deflection angle.

6. The ophthalmologic apparatus of claim 1, wherein the optical scanner operates in at least one of a first range where a deflection angle varies linearly with respect to changes in time, and a second range where the deflection angle varies non-linearly with respect to the changes in time.

7. An ophthalmologic apparatus, comprising:
an acquisition unit including an optical scanner capable of deflecting light in a predetermined deflection angle range and configured to acquire data of a subject's eye by performing A-scan on the subject's eye using optical coherence tomography by measurement light deflected by the optical scanner; and
a controller configured to cause the acquisition unit to perform A-scan based on a deflection operation state of the optical scanner,
wherein the controller is configured to cause the acquisition unit to perform A-scan so that intervals between the deflection angles are substantially equal.

8. The ophthalmologic apparatus of claim 7, wherein the optical scanner operates in at least one of a first range where a deflection angle varies linearly with respect to changes in time, and a second range where the deflection angle varies non-linearly with respect to the changes in time.

9. A method of controlling an ophthalmologic apparatus including an optical scanner capable of deflecting light in a predetermined deflection angle range, the method comprising:
an acquisition step of acquiring data of a subject's eye by performing A-scan on the subject's eye using optical coherence tomography by measurement light deflected by the optical scanner; and
a control step of performing A-scan based on a deflection operation state of the optical scanner, wherein
the control step includes:
an operation information acquisition step that acquires operation information representing a deflection angle of the optical scanner;
a determination step that determines whether or not the deflection angle is a predetermined deflection angle based on the acquired operation information; and
a performing step that performs A-scan when it is determined that the deflection angle is the predetermined deflection angle.

10. The method of controlling the ophthalmologic apparatus of claim 9, wherein
the control step performs A-scan based on timing information of the A-scan stored in advance.

11. The method of controlling the ophthalmologic apparatus of claim 10, wherein
the timing information includes timing information of A-scan with reference to a reference timing of deflection operation of the optical scanner, and
the control step performs A-scan at a timing specified by the timing information.

12. The method of claim 9, wherein the optical scanner operates in at least one of a first range where a deflection angle varies linearly with respect to changes in time, and a second range where the deflection angle varies non-linearly with respect to the changes in time.

13. A method of controlling an ophthalmologic apparatus including an optical scanner capable of deflecting light in a predetermined deflection angle range, the method comprising:
an acquisition step of acquiring data of a subject's eye by performing A-scan on the subject's eye using optical coherence tomography by measurement light deflected by the optical scanner; and
a control step of performing A-scan based on a deflection operation state of the optical scanner, wherein
the control step performs A-scan so that intervals between the deflection angles are substantially equal.

14. The method of claim 13, wherein the optical scanner operates in at least one of a first range where a deflection angle varies linearly with respect to changes in time, and a second range where the deflection angle varies non-linearly with respect to the changes in time.

15. A method of controlling an ophthalmologic apparatus including an optical scanner capable of deflecting light in a predetermined deflection angle range, the method comprising:
an acquisition step of acquiring data of a subject's eye by performing A-scan on the subject's eye using optical coherence tomography by measurement light deflected by the optical scanner; and a control step of performing A-scan based on a deflection operation state of the optical scanner, wherein the control step performs A-scan so that intervals between projection positions of the measurement light on the subject's eye are substantially equal.

16. The method of claim 15, wherein the optical scanner operates in at least one of a first range where a deflection angle varies linearly with respect to changes in time, and a second range where the deflection angle varies non-linearly with respect to the changes in time.

* * * * *